United States Patent
Ren et al.

(10) Patent No.: US 12,295,771 B2
(45) Date of Patent: May 13, 2025

(54) SYSTEMS AND METHODS FOR MEASURING DEFLECTION OF FOAM BREAST COMPRESSION PADDLE

(71) Applicant: HOLOGIC, INC., Marlborough, MA (US)

(72) Inventors: Baorui Ren, Marlborough, MA (US); Kenneth Defreitas, Marlborough, MA (US); Alan Rego, Marlborough, MA (US); Christopher Ruth, Marlborough, MA (US); Andrew P. Smith, Marlborough, MA (US); Zhenxue Jing, Marlborough, MA (US); Jay A. Stein, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 216 days.

(21) Appl. No.: 17/910,311

(22) PCT Filed: Mar. 22, 2021

(86) PCT No.: PCT/US2021/023457
§ 371 (c)(1),
(2) Date: Sep. 8, 2022

(87) PCT Pub. No.: WO2021/194957
PCT Pub. Date: Sep. 30, 2021

(65) Prior Publication Data
US 2023/0121488 A1 Apr. 20, 2023

Related U.S. Application Data

(60) Provisional application No. 63/000,790, filed on Mar. 27, 2020.

(51) Int. Cl.
*A61B 6/50* (2024.01)
*A61B 6/00* (2024.01)
(Continued)

(52) U.S. Cl.
CPC .............. *A61B 6/502* (2013.01); *A61B 6/025* (2013.01); *A61B 6/0414* (2013.01); *A61B 6/463* (2013.01);
(Continued)

(58) Field of Classification Search
CPC ..... A61B 6/502; A61B 6/0435; A61B 6/0414; A61B 6/032; A61B 6/025; A61B 6/5217;
(Continued)

(56) References Cited

U.S. PATENT DOCUMENTS

| 4,744,099 A | 5/1988 | Huettenrauch et al. |
| 5,474,072 A | 12/1995 | Shmulewitz |

(Continued)

FOREIGN PATENT DOCUMENTS

| DE | 10 20160217599 | 3/2018 |
| JP | 2006-519625 A | 8/2006 |

(Continued)

OTHER PUBLICATIONS

Mawdsley, Gordon et al., "Accurate estimation of compressed breast thickness in mammography", Medical physics, 2009, 6 (2), pp. 577-586.

(Continued)

*Primary Examiner* — Irakli Kiknadze
(74) *Attorney, Agent, or Firm* — Merchant & Gould P.C.

(57) ABSTRACT

A method of imaging a breast compressed with a foam paddle includes emitting an x-ray energy from an x-ray source towards the breast and the foam paddle having a plurality of upper markers and a plurality of lower markers, wherein the plurality of lower markers are movable relative to the upper markers. The x-ray energy is detected at a detector disposed opposite the breast from the x-ray source. An image of the compressed breast is generated based on the detected x-ray energy. At least one of the plurality of upper (Continued)

markers and at least one of the plurality of lower markers is identified in the image. A thickness of the compressed breast at a plurality of thickness locations is determined, wherein each of the plurality of thickness locations corresponds to at least one of the plurality of lower markers.

22 Claims, 19 Drawing Sheets

(51) Int. Cl.
    *A61B 6/02*     (2006.01)
    *A61B 6/04*     (2006.01)
    *A61B 6/46*     (2024.01)
    *A61B 90/00*     (2016.01)

(52) U.S. Cl.
    CPC .......... *A61B 6/5217* (2013.01); *A61B 6/5252* (2013.01); *A61B 6/544* (2013.01); *A61B 90/39* (2016.02); *A61B 6/488* (2013.01); *A61B 2090/3966* (2016.02)

(58) Field of Classification Search
    CPC ..... A61B 6/5258; A61B 6/4417; A61B 6/461; A61B 8/0825; A61B 2090/3966; A61B 5/1075; A61B 2090/3908; A61B 6/5205; A61B 2090/3937; A61B 6/583; A61B 6/582; A61B 6/4258; A61B 6/544; A61B 6/542; A61B 6/405; A61B 6/4233; A61B 6/482; A61B 6/466; A61B 6/02; A61B 6/4035; A61B 6/4291; A61B 6/4085; A61B 6/463; A61B 90/39; A61B 6/5252; A61B 6/545; A61B 6/488; A61B 6/0492; A61B 6/563; A61B 6/5264; G06T 11/006; G06T 2207/30068; G06T 2207/10112; G06T 2207/30004; G06T 11/003; G16H 50/50; G16H 50/30; G01T 1/1615; G01T 1/1642; G01T 1/1611; G01N 23/046; G01N 2223/419; G01N 2223/612; G01N 2223/423
    USPC ............................. 378/21, 37–40, 50, 51, 62
    See application file for complete search history.

(56) References Cited

U.S. PATENT DOCUMENTS

| | | | |
|---|---|---|---|
| 5,506,877 | A | 4/1996 | Niklason et al. |
| 6,577,702 | B1 | 6/2003 | Lebovic |
| 8,401,145 | B1 | 3/2013 | Boutte |
| 8,768,026 | B2 | 7/2014 | Ren et al. |
| 9,883,846 | B2 | 2/2018 | Son |
| 11,364,000 | B2 | 6/2022 | Defreitas et al. |
| 11,426,132 | B2 | 8/2022 | DeFreitas |
| 11,596,368 | B2 | 3/2023 | Stein |
| 11,751,824 | B2 | 9/2023 | Defreitas et al. |
| 11,832,783 | B2 | 12/2023 | Defreitas et al. |
| 2003/0007597 | A1 | 1/2003 | Higgins |
| 2003/0099325 | A1 | 5/2003 | Galkin |
| 2004/0101095 | A1 | 5/2004 | Jing et al. |
| 2004/0156472 | A1 | 8/2004 | Galkin |
| 2004/0218727 | A1 | 11/2004 | Shoenfeld |
| 2005/0008117 | A1 | 1/2005 | Livingston |
| 2006/0050844 | A1 | 3/2006 | Galkin |
| 2006/0126794 | A1 | 6/2006 | Hermann |
| 2007/0280412 | A1 | 12/2007 | DeFreitas et al. |
| 2008/0045833 | A1 | 2/2008 | Defreitas et al. |
| 2009/0135997 | A1 | 5/2009 | DeFreitas et al. |
| 2009/0268865 | A1 | 10/2009 | Ren et al. |
| 2010/0067659 | A1 | 3/2010 | Bush |
| 2010/0179604 | A1 | 7/2010 | Campagna |
| 2012/0114096 | A1 | 5/2012 | Lebovic et al. |
| 2013/0129039 | A1 | 5/2013 | DeFreitas |
| 2014/0177791 | A1 | 6/2014 | Otokuni et al. |
| 2014/0226786 | A1 | 8/2014 | Goossen et al. |
| 2015/0250432 | A1 | 9/2015 | Savagian |
| 2015/0305693 | A1 | 10/2015 | Galambos McLaughlin |
| 2016/0029979 | A1* | 2/2016 | Mawdsley ............ A61B 6/502 378/207 |
| 2016/0081633 | A1 | 3/2016 | Stango |
| 2016/0183898 | A1 | 6/2016 | Cormican |
| 2016/0206229 | A1 | 7/2016 | Arai et al. |
| 2017/0251991 | A1 | 9/2017 | Wang et al. |
| 2017/0340303 | A1 | 11/2017 | Stango et al. |
| 2018/0125437 | A1 | 5/2018 | Stango et al. |
| 2021/0015435 | A1 | 1/2021 | DeFreitas |
| 2021/0030375 | A1 | 2/2021 | Defreitas et al. |
| 2021/0361246 | A1 | 11/2021 | Defreitas et al. |
| 2022/0361828 | A1 | 11/2022 | Defreitas et al. |
| 2023/0022003 | A1 | 1/2023 | Defreitas et al. |
| 2024/0065649 | A1 | 2/2024 | DeFreitas |

FOREIGN PATENT DOCUMENTS

| | | |
|---|---|---|
| JP | 2009-178227 A | 8/2009 |
| JP | 2011-206436 | 10/2011 |
| JP | 2011-206438 | 10/2011 |
| JP | 2012-231888 A | 11/2012 |
| JP | 2014-073294 A | 4/2014 |
| JP | 2017-176509 A | 10/2017 |
| WO | 2001/066013 | 9/2001 |
| WO | 2007/095330 | 8/2007 |
| WO | 2014/176445 | 10/2014 |
| WO | 2015/018848 | 2/2015 |
| WO | 2016/172294 | 10/2016 |
| WO | 2019/227042 A1 | 11/2019 |
| WO | 2019/227044 A1 | 11/2019 |
| WO | 2019/227051 A2 | 11/2019 |

OTHER PUBLICATIONS

Petru, M., et al "Measurement and Numerical Modeling of Mechanical Properties of Polyurethane Foams", Aspects of Polyurethanes, 2017, pp. 73-109.

Dibble et al., "Mammography with breast cushions", Women's Health Issues, Elsevier, vol. 15, No. 2, Mar. 1, 2005, 9 pages.

International Search Report and Written Opinion of the International Searching Authority for International Patent Application No. PCT/US2021/023457 mailed Jul. 6, 2021, 11 pages.

PCT International Preliminary Report on Patentability in International Patent Application No. PCT/US2021/023457 mailed Oct. 6, 2022, 9 pages.

* cited by examiner

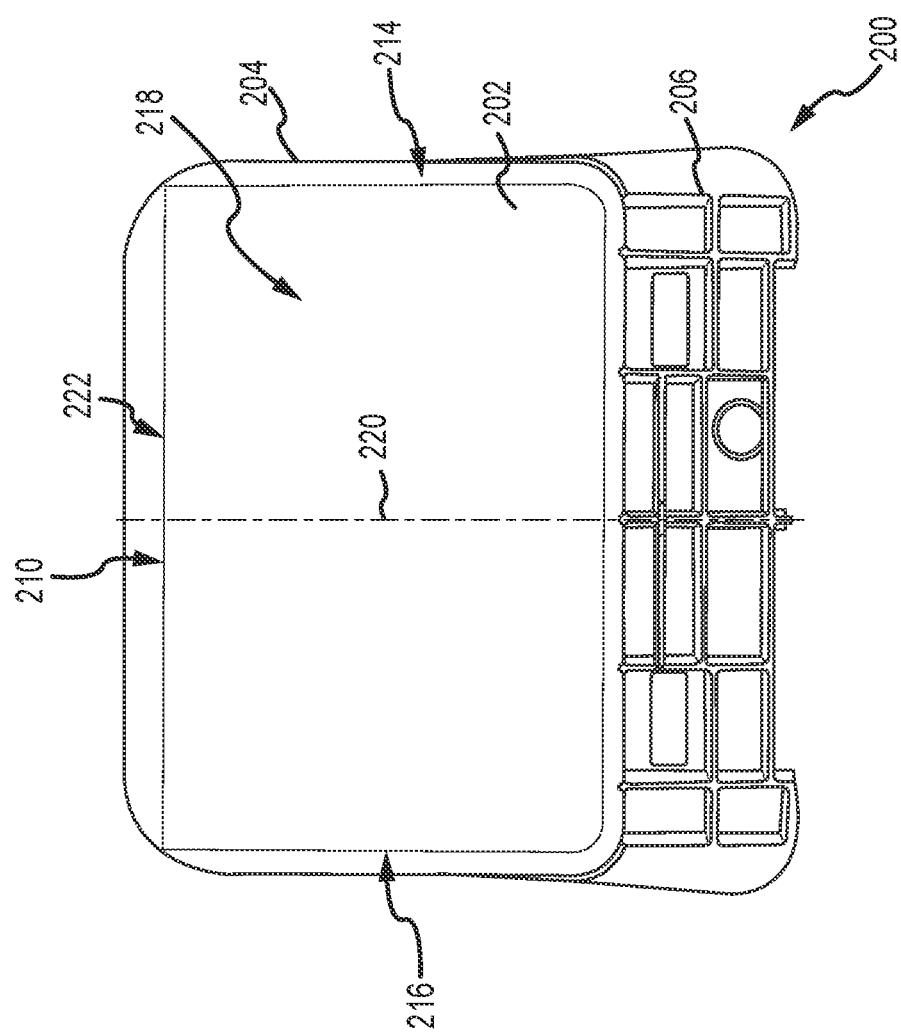

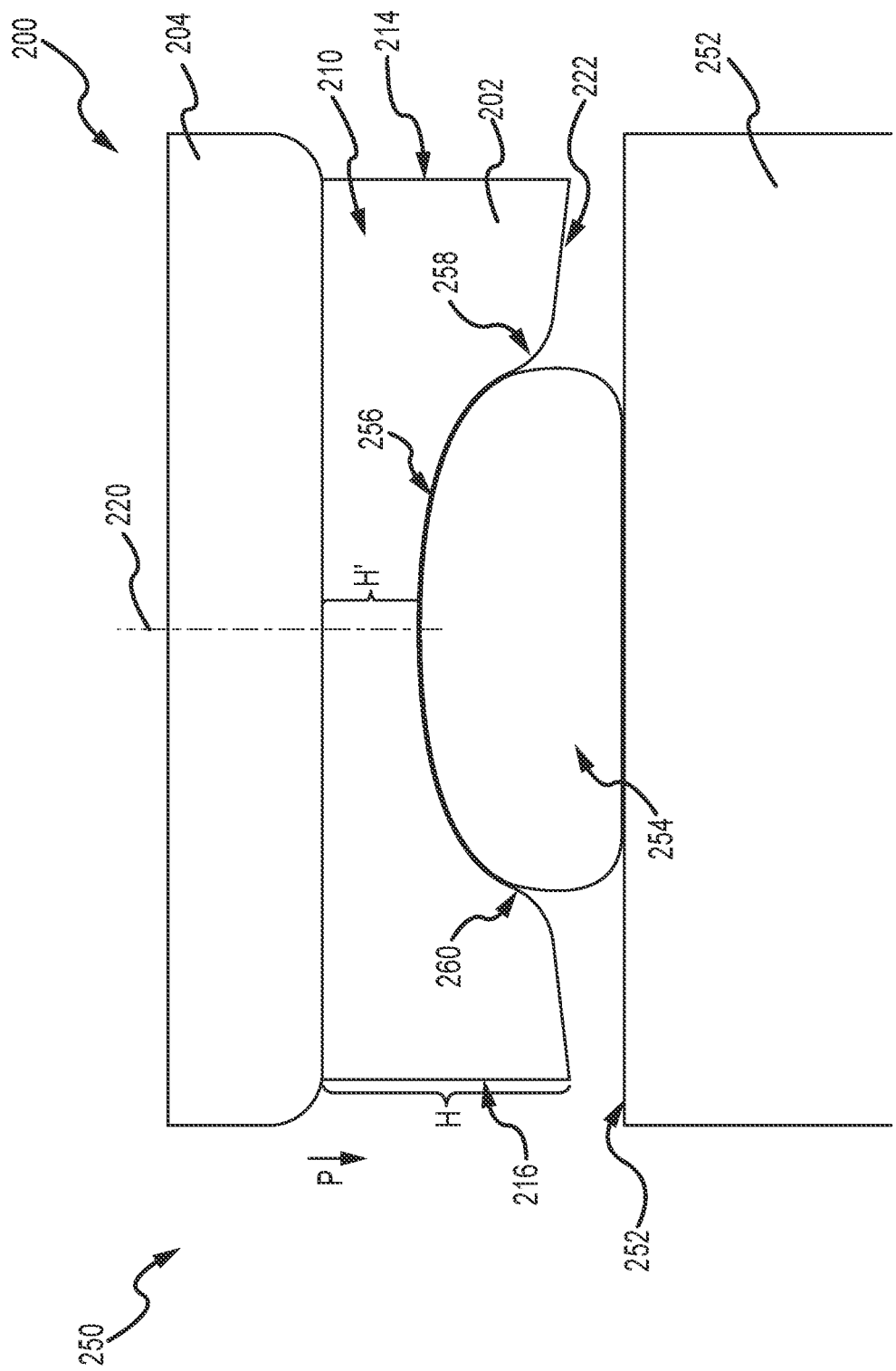

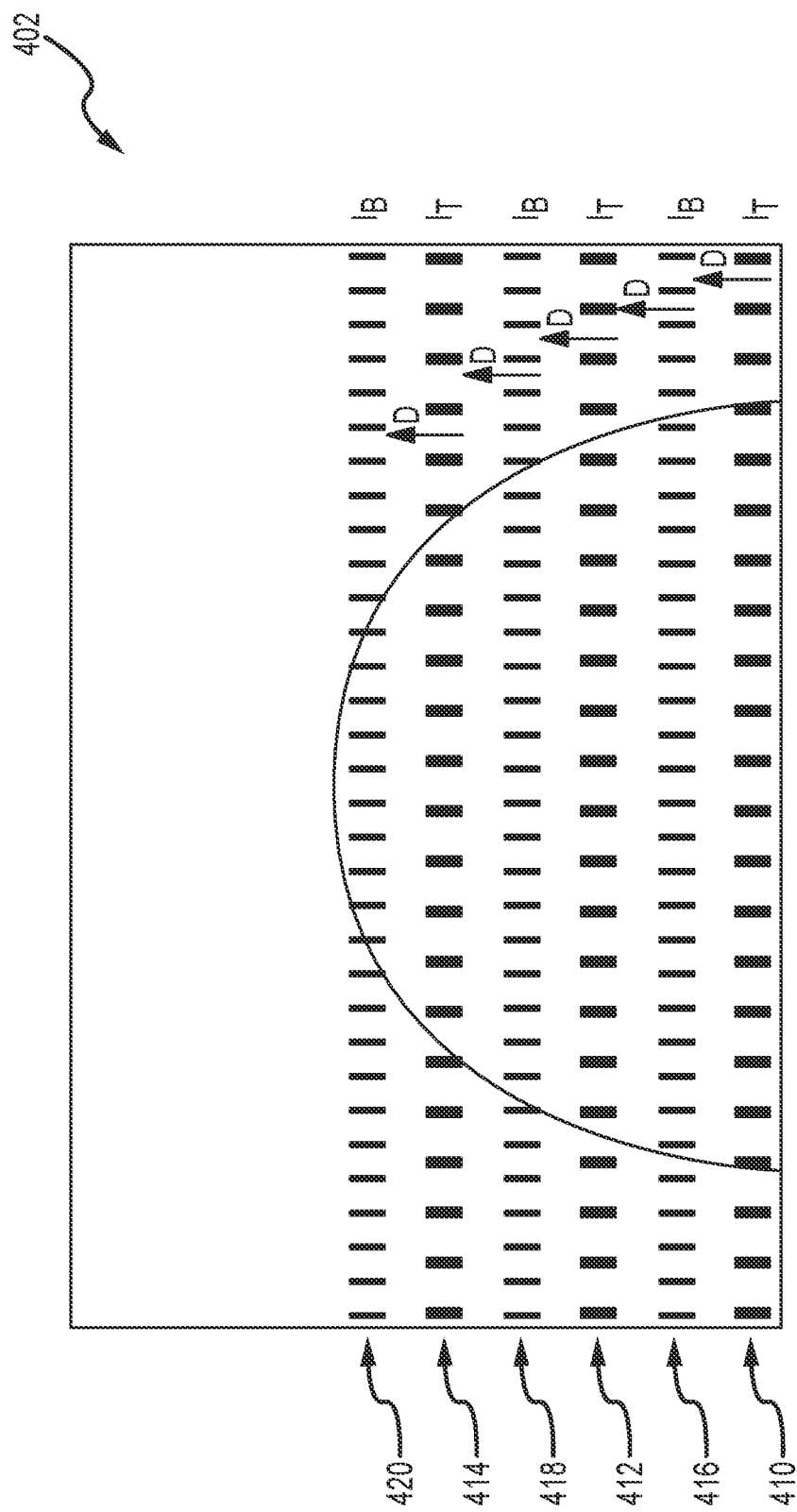

SYSTEMS AND METHODS FOR MEASURING DEFLECTION OF FOAM BREAST COMPRESSION PADDLE

CROSS-REFERENCE TO RELATED APPLICATIONS

This application is a National Stage Application of PCT/US2021/023457, filed on Mar. 22, 2021, which claims the benefit of priority to U.S. Provisional Patent Application Ser. No. 63/000,790, filed Mar. 27, 2020, the entire disclosures of which are incorporated by reference in their entireties. To the extent appropriate, a claim of priority is made to each of the above disclosed applications.

BACKGROUND

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue. This discomfort has led to the development of compression paddles having flexible features, e.g., plastic sheets, flexible meshes, foam compressive materials, etc. These flexible materials present unique challenges to properly image the breast. In existing imaging systems that utilize flat, rigid compression paddles, thickness of the compressed breast may be fairly easily determined by measuring or calculating a height of the compression paddle above a breast support platform. The use of flexible materials to stabilize a breast, however, make such simple calculations impossible.

SUMMARY

In one aspect, the technology relates to a method of imaging a breast compressed with a foam paddle, the method including: emitting an x-ray energy from an x-ray source towards the breast and the foam paddle having a plurality of upper markers and a plurality of lower markers, wherein the plurality of lower markers are movable relative to the upper markers; detecting the x-ray energy at a detector disposed opposite the breast from the x-ray source; generating an image of the compressed breast based on the detected x-ray energy; identifying, in the image, at least one of the plurality of upper markers and at least one of the plurality of lower markers; and determining a thickness of the compressed breast at a plurality of thickness locations, wherein each of the plurality of thickness locations corresponds to at least one of the plurality of lower markers. In an example, determining the thickness includes calculating a distance, in the image, between a first upper marker of the plurality of upper markers and an image-adjacent first lower marker of the plurality of lower markers. In another example, determining the thickness includes determining a characteristic, in the image, of at least one lower marker of the plurality of lower markers. In yet another example, determining the thickness includes calculating a distance, in the image, between a first upper marker of the plurality of upper markers and a second upper marker of the plurality of upper markers. In still another example, determining the thickness includes calculating a distance, in the image, between a first lower marker of the plurality of lower markers and a second lower marker of the plurality of lower markers.

In another example of the above aspect, the x-ray energy includes a scout exposure. In another example, the method further includes calculating an automatic exposure control based at least in part on the determination of the thickness. In yet another example, the method includes emitting an imaging x-ray energy based at least in part on the calculated automatic exposure control.

In another example of the above aspect, the method includes modeling a difference in at least two thickness locations of the plurality of thickness locations; and applying attenuation to the image based at least in part of the modeled difference.

In another example of the above aspect, the method includes performing a tomosynthesis imaging procedure; obtaining a set of tomosynthesis images of the compressed breast from the tomosynthesis imaging procedure; and identifying a breast boundary in at least one tomosynthesis image of the set of tomosynthesis images. In an example, identifying the breast boundary is based at least in part on the determination of the thickness. In yet another example, the method includes displaying at least one tomosynthesis image of the set of tomosynthesis images; and displaying, on the displayed at least one tomosynthesis image of the set of tomosynthesis images, a feature indicative of the breast boundary. In still another example, the displayed at least one tomosynthesis image includes an uppermost tomosynthesis image of the breast.

In another example of the above aspect, the method includes calculating an x-ray imaging dose based at least in part on the determination.

In another example of the above aspect, the method includes processing the image; identifying at least one reference marker of at least one of the plurality of upper markers and the plurality of lower markers; applying a negative signal to the identified reference marker, wherein the application results in a corrected image; and displaying the corrected image. In another example, applying the negative signal includes adjusting a pixel count at the identified reference marker.

In another aspect, the technology relates to a paddle for compressing a breast, the paddle including: a foam profile comprising an upper surface, a lower surface, and a front wall; a plurality of upper markers disposed proximate the upper surface, wherein the plurality of upper markers are disposed a first distance from the front wall; and a plurality of lower markers disposed proximate the lower surface, wherein the plurality of lower markers are disposed a second distance from the front wall. In an example, the paddle includes a rigid substrate, wherein the foam profile is secured to the rigid substrate at the upper surface, and wherein the plurality of upper markers are disposed between the rigid substrate and the foam profile. In another example, the plurality of lower markers are disposed within the foam profile. In yet another example, the plurality of markers are configured to move when the lower surface of the paddle is acted upon by an upward force. In still another example, the plurality of upper markers are configured to remain stationary when the lower surface of the paddle is acted upon by the upward force. In another example, the paddle includes a bottom foam profile secured to the foam profile, wherein the plurality of lower markers are disposed between the bottom foam profile and the foam profile.

BRIEF DESCRIPTION OF THE DRAWINGS

FIGS. 2A-2C are various views of a breast compression paddle having a foam compressive element.

FIG. 2D is a front view of the breast compression paddle of FIGS. 2A-2C compressing a breast.

FIG. 4B depicts a top view of an image of the paddle of FIG. 4A, in an uncompressed position.

DETAILED DESCRIPTION

Paddles utilizing foam compressive material reduce patient discomfort during imaging procedures, which may persuade more women to have regular examinations, thus leading to early cancer diagnosis. Due to this improved comfort, patients may also move less during imaging procedures, which leads to improved image results. Paddles utilizing foam compressive material, however, produce a breast shape very different from that of a breast compressed with a conventional rigid-type paddle. More specifically, when compressed with a foam compressive element, the resulting compressed breast does not have a uniform thickness across the field of view. Thus, while paddles utilizing foam compressive elements are more comfortable, such paddles introduce myriad challenges to how a breast imaging system (e.g., a mammography, tomosynthesis, or combination mammography/tomosynthesis system) takes exposures and produces images of diagnostically-relevant quality.

The technologies described herein provide methods to accurately measure local breast and foam thicknesses under the foam compressive material for the entire field of view. The technology contemplates systems and methods that measure local thickness at discrete locations below the paddle. With this information on breast thickness across the entire breast known, automatic exposure control (AEC) and x-ray dose may be more accurately calculated. Further, image processing and display may be improved. In an example of the former, since using foam compressive elements results in a breast that lacks a uniform thickness, the resulting x-ray image would appear non-flat after standard image processing, making it more difficult for the radiologist to review the image. In a particular example of the latter, accurate measurement of breast thickness allows the breast boundary to be determined, so that areas outside of the boundary (e.g., in discrete images of a set of tomosynthesis images) may be excluded from a subsequent review. Thus, these technologies are critical to make viable paddles utilizing a foam compressive material.

Figure 1A:
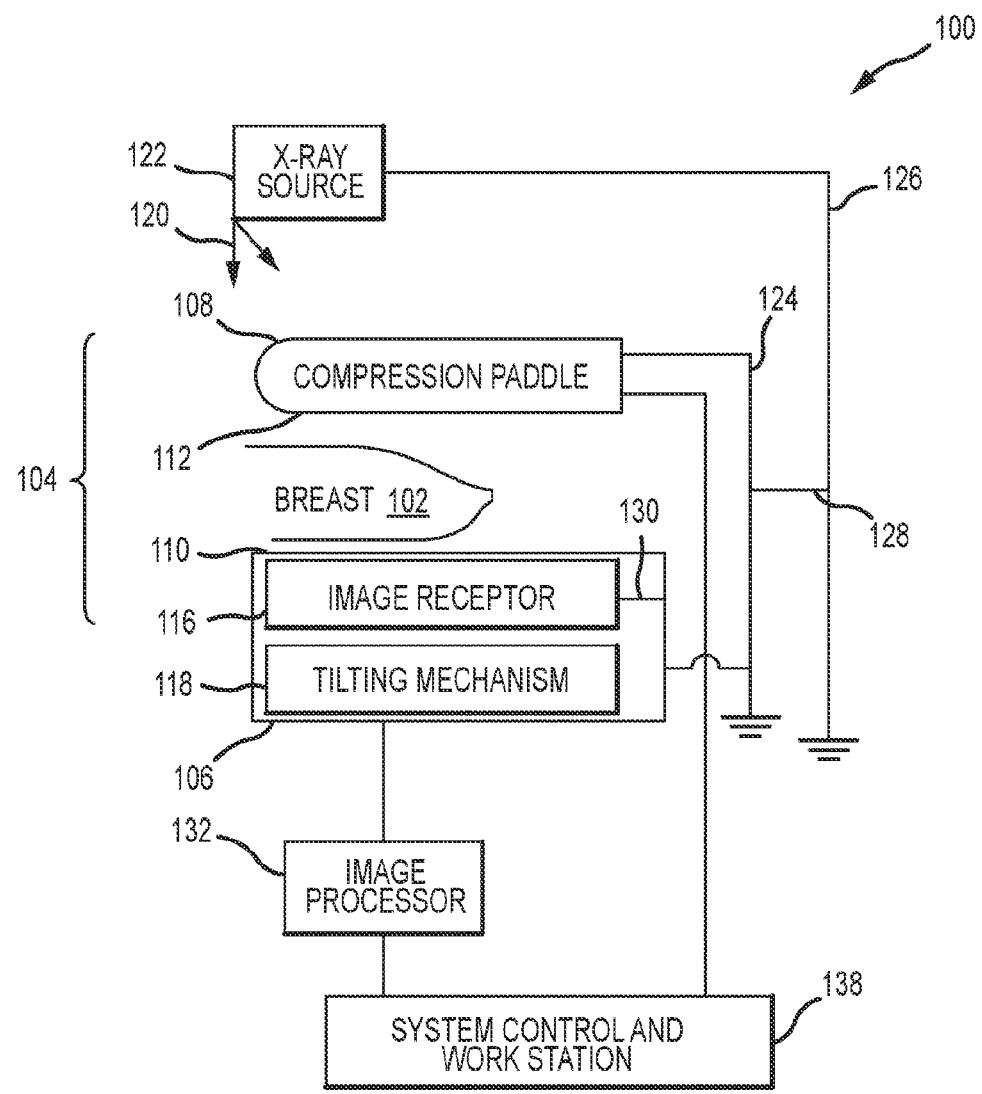
FIG. 1A is a schematic view of an exemplary imaging system.
Figure 1B:
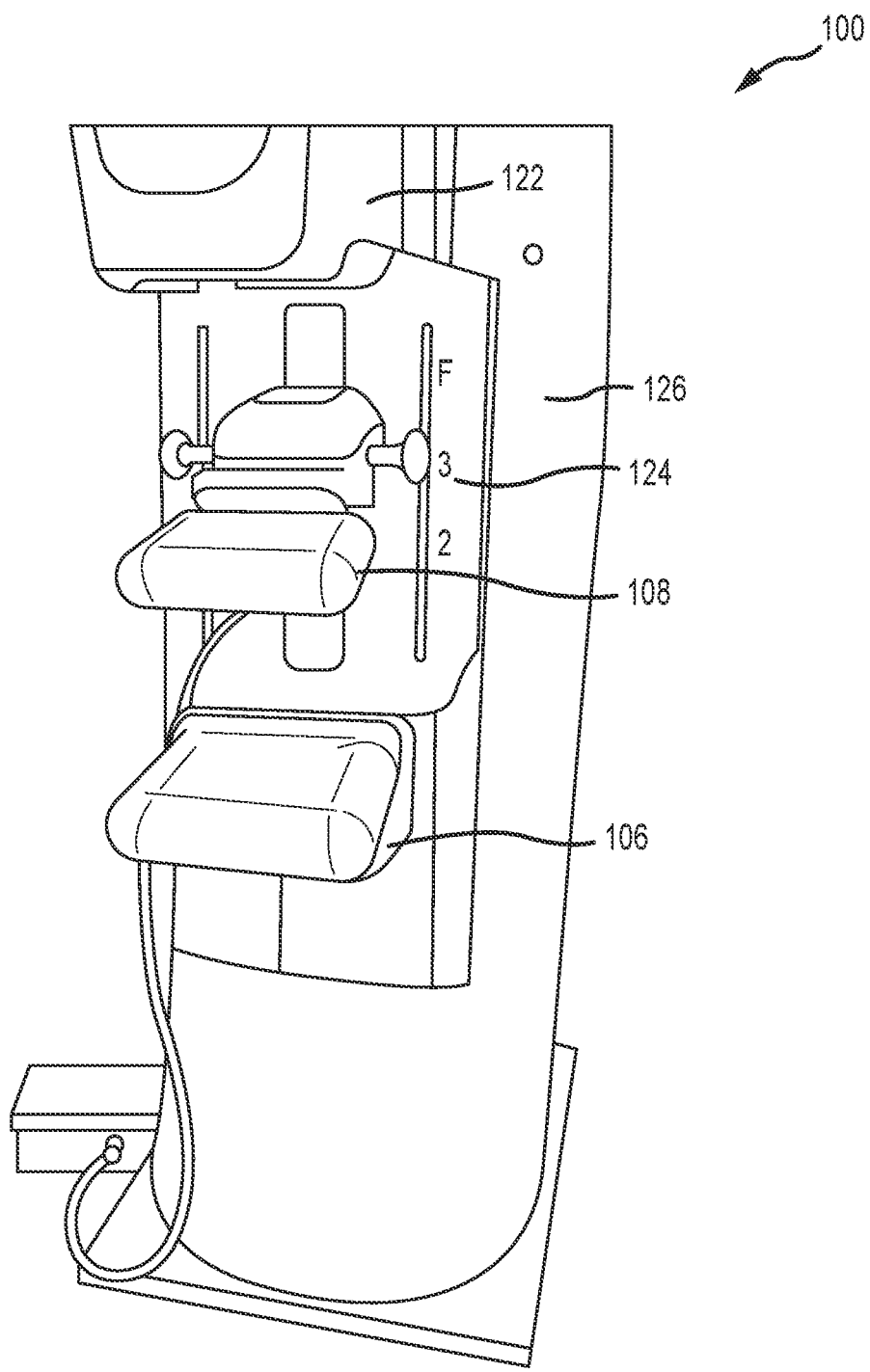
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 immobilizes a patient's breast 102 for x-ray imaging (either or both of mammography and tomosynthesis) via a breast compression immobilizer unit 104 that includes a static breast support platform 106 and a moveable compression paddle 108. The breast support platform 106 and the compression paddle 108 each have a compression surface 110 and 112, respectively, that move towards each other to compress and immobilize the breast 102. In known systems, the compression surface 110, 112 is exposed so as to directly contact the breast 102. The platform 106 also houses an image receptor 116 and, optionally, a tilting mechanism 118, and optionally an anti-scatter grid. The immobilizer unit 104 is in a path of an imaging beam 120 emanating from x-ray source 122, such that the beam 120 impinges on the image receptor 116.

The immobilizer unit 104 is supported on a first support arm 124 and the x-ray source 122 is supported on a second support arm 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112. This can cause discomfort to the patient.

To improve comfort for the patient, compression paddles utilizing foam compressive materials have been developed. Compression paddles utilizing foam compressive materials are described generally in PCT International Patent Application Nos. PCT/US2019/033998, PCT/US2019/034001, and PCT/US2019/034010, all filed May 24, 2019, the disclosures of which are hereby incorporated by reference herein in their entireties. Such paddles stabilize and compress slightly the breast, while reducing discomfort associated with compression paddles having only rigid compressive surfaces.

Figure 2A:
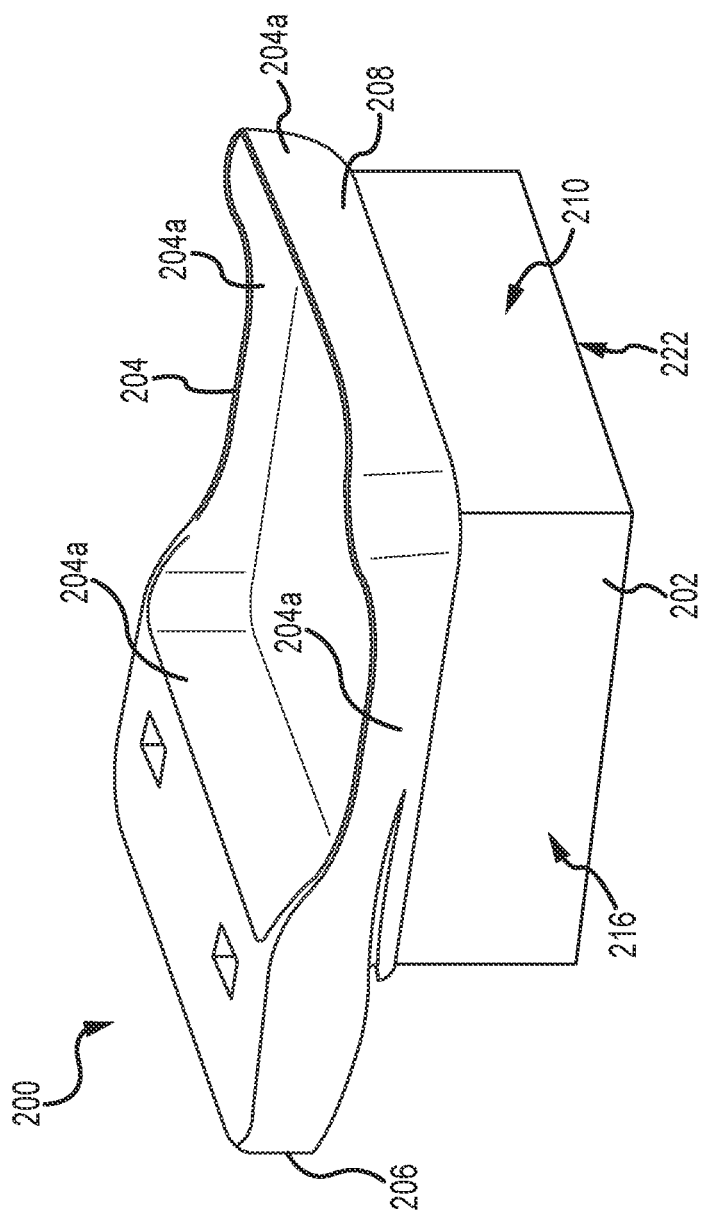
Figure 2B:
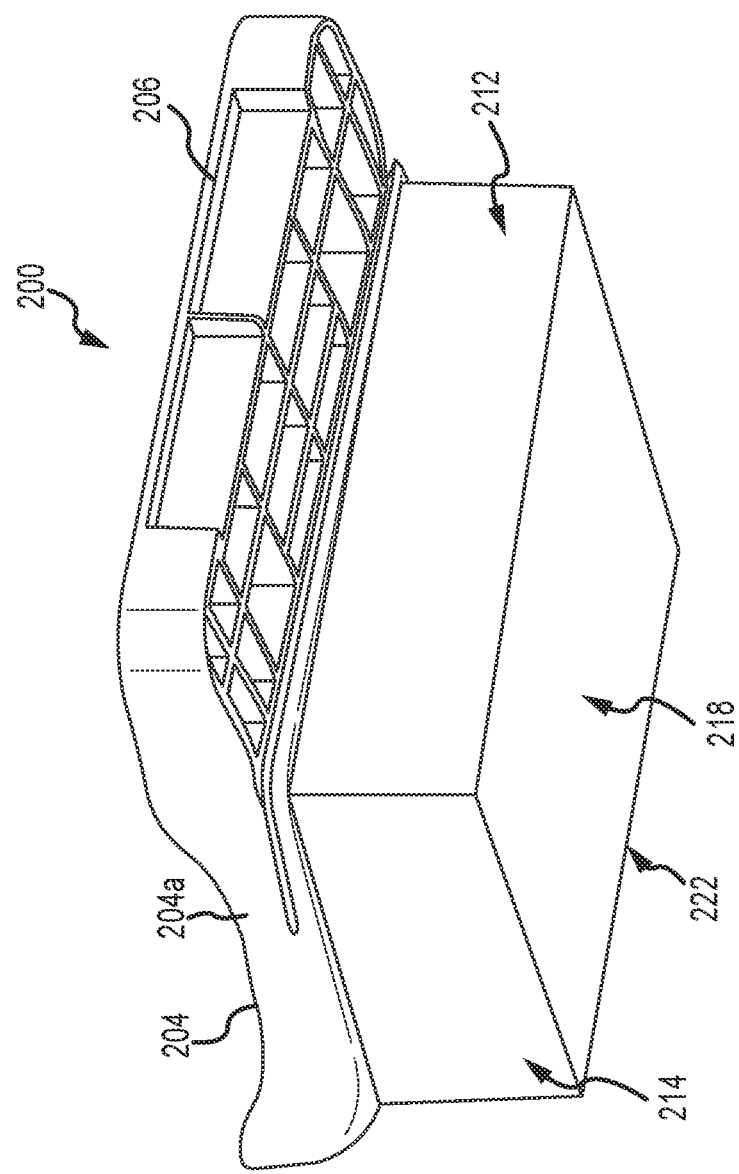

FIGS. 2A-2C are various views of one example of a breast compression paddle 200 having a foam compressive element 202 secured to a rigid substrate 204. FIGS. 2A-2C are described concurrently. The paddle 200 includes a bracket portion 206, generally integral with the substrate 204 for connecting the paddle to compression arm of an imaging system. The paddle 200 also includes a leading face 208, opposite the bracket portion 206, which is disposed proximate a chest wall of a patient during compression and imaging procedures. In examples, the substrate may be rigid. As used herein, the term "rigid" does not imply that the substrate 204 is free from bending during compression of a breast, rather that the substrate 204 displays greater resistance to bending or deformation than the foam compressive element 202 secured to a bottom of the substrate 204. Raised walls 204a provide additional rigidity.

The foam compressive element 202 may be secured to a bottom surface of the substrate 204 with a chemical adhesive. In other example, an upper surface of the compressive element may be a rigid plastic or other material to which the foam compressive element 202 is secured. A plurality of bolts, hooks, or other mechanical fasteners (not shown) may be used to connect this rigid plastic to the rigid substrate 204 of the paddle 200. If such mechanical fasteners are used, it may be desirable to dispose said fasteners away from areas of the foam compressive material 202 that are expected to compress against a breast, so as to avoid pressure points and resulting discomfort associated therewith, as well as to prevent artifacts from appearing in any resulting x-ray images.

The foam compressive element 202 includes a number of edge surfaces. A leading edge surface 210 is disposed proximate the leading face 208 of the substrate 204 so as to be disposed proximate the chest wall of a patient during compression and imaging procedures. A trailing edge surface 212 is disposed opposite the leading edge surface 210, proximate the bracket portion 206. Lateral edge surfaces 214, 216 are also depicted. In general, these lateral edge surfaces 214, 216 may be depicted as inner or outer lateral edge surfaces, consistent with terminology typically used to describe inner and outer sides of the breast. Of course, a person of skill in the art will recognize that the same compression paddle 200 may be used to compress either breast, one at a time, which would effectively change the application of the terms "inner" and "outer" to the lateral edge surfaces of the foam compressive material 202. Further, a mid-plane 220 is disposed between the lateral edge surfaces 214, 216, at an approximate midpoint thereof. The mid-plane 220 is disposed substantially orthogonal to a compressive surface 218 that is disposed on an underside of the foam compressive material 202. Portions of the compressive surface 218 will contact the breast during compression. In another example, the foam compressive material 202 may be covered with a biocompatible cover, which may protect the foam compressive material 202 from absorbing bodily fluids. In examples, the may be disposable or cleanable. To improve the patient experience, the cover may be manufactured of a soft material where it contacts the patient. To prevent fluid transfer into the foam compressive material 202, an opposite plastic side may contact the foam compressive material 202. An interface 222 is located where the compressive surface 218 meets the leading edge surface 210. The shape of the interface 222 during compression aids in defining the foam compressive material 202 and the function thereof.

FIG. 2D is a front view of a compression system 250 for an imaging system. The compression system 250 includes a first compression element in the form of a compression paddle 200 having a rigid substrate 204 and a foam compressive element 202 secured thereto. A second compression element, in this case a breast support platform 252 is also depicted. A breast 254 resting on an upper surface 256 of the breast support platform 252 is also depicted. During use, the breast 254 is compressed by application of a force F by the compression paddle 200. The foam compressive material 202 deforms and conforms to the contours of the breast 254 as compression increases. As such, as the force F is increased, compression of both the breast 254 and foam compressive material 202 occurs. This compression may be defined by the percentage of compression of the foam compressive material 202 proximate the mid-plane 220 at the leading edge surface 210, when the breast 254 is substantially centered along the mid-plane 220. In other examples, the contours of the interface 222 may define the compression of the foam compressive material 202.

As described above, the foam compressive material 202 has an uncompressed height H of the front edge surface 210. In examples, the uncompressed height H at the front edge surface 210 may be about one inch to about two inches. In another example, the uncompressed height H may be about two inches to about three inches. In another example, the uncompressed height H may be in excess of about three inches. It has been determined through testing that an uncompressed height H of about three inches is sufficient for compression of a significant number of breast sizes, from small to large. Prior to a tomosynthesis imaging procedure, the breast 254 may be compressed to an imaging condition, which in one example, is a condition to sufficiently stabilize the breast and compress the breast somewhat. Unlike in prior systems where compression with a hard compression paddle results in significant flattening of the breast, the imaging condition to which the breast is compressed need only be to a thickness where the resultant tomosynthesis images are a manageable number. Such a manageable number may be a diagnostically significant number, such that the resulting breast image slices may provide sufficient distinction between slices, but without having such a large number of images, which would necessitate significantly more review time by a clinician.

In examples, this imaging condition of the breast 254 is reached prior to complete compression of the foam compressive material 202 at the front edge surface 210. FIG. 2D depicts compression of the foam compressive material to a maximum amount required for the breast 254 to be in the imaging condition. For illustrative purposes, FIG. 2D depicts the breast 254 centered on the mid-plane 220 of the foam compressive material 202. Thus, a portion of the foam compressive element 202 at this position is not completely compressed and is depicted in FIG. 2D as incompletely compressed height H'. This incompletely compressed height H' is the portion of the foam compressive material 202, measured at the leading edge surface 210 that, while the most compressed portion of the foam compressive material 202, may still be compressed further if further force was applied to the breast 254. In examples, the imaging condition of the breast may be reached when only a portion of the foam compressive material 202 reaches a completely compressed height H'. This completely compressed height H' changes (i.e., increases) as distance from the chest wall increases. This is the result of the shape of a breast and the properties of the foam compressive material.

The shape of the interface 222 may define the compression of the foam compressive material 202. Unlike prior art thin foam pads, where an interface between the compressive surface and a leading edge surface is pressed substantially flat along the entire length of the breast, the foam compressive material 202 of the present technology maintains a curved shaped along much of the entire breast 254. The interface 222, for example, defines a generally smooth curvature 256 from a first contact point 258 proximate an inner side of the breast 254 to a second contact point 260 proximate an outer side of the breast 254. Prior art thin foam pads, however, are almost flat from a first contact point to a second contact point.

Figure 3B:
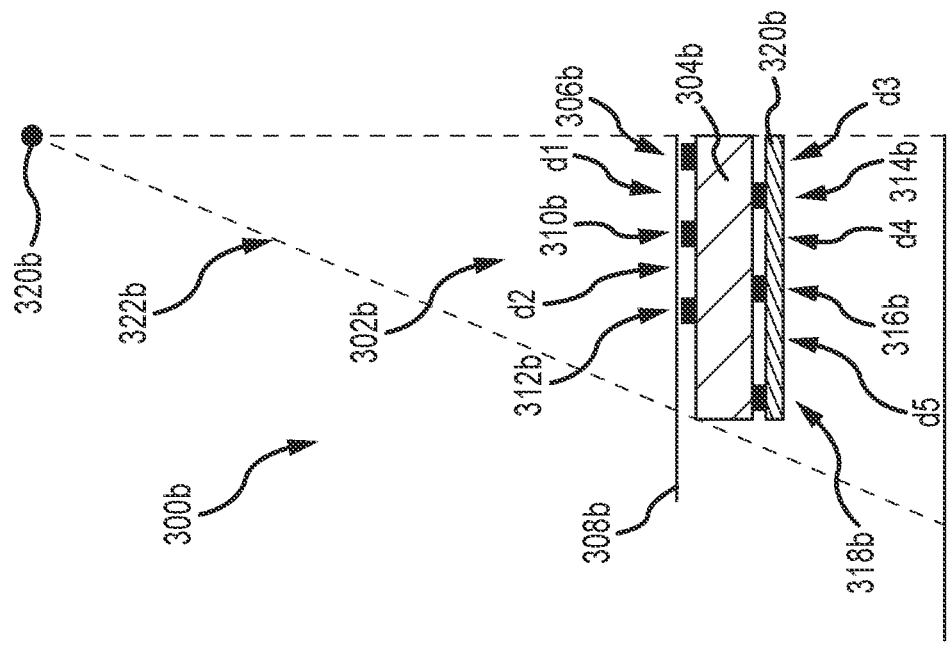
FIGS. 3A and 3B depict partial side views of imaging systems having paddles utilizing foam compressive elements with markers thereon.
Figure 3A:
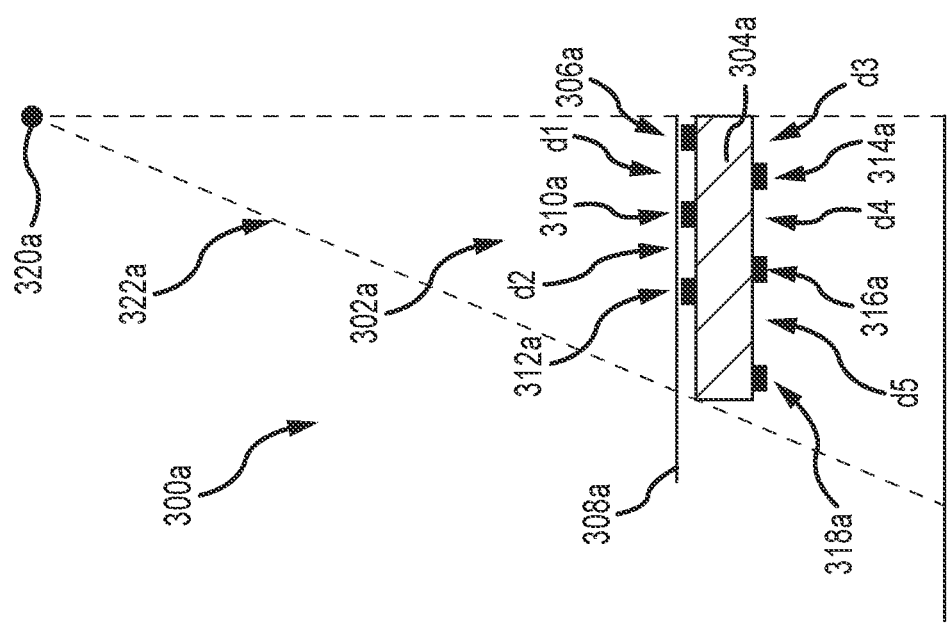

FIGS. 3A and 3B depict partial side views of imaging systems 300 having paddles 302 utilizing foam compressive materials 304 with a plurality of markers thereon. The plurality of markers, arranged in multiple rows above and below the foam compressive material 304 (as described in more detail herein), allow for the detection of non-uniform thickness of the compressed breast. Unless otherwise noted, suffixes depicted in FIGS. 3A and 3B correspond to the specific features described without suffixes in the description of those figures. Each paddle 302 includes a rigid substrate 308 and a foam compressive material 304 secured to a bottom surface thereof. In the figures, the rigid substrate 308 is depicted spaced apart from the foam compressive material 304, but this is for illustrative purposes only. Secured between the rigid substrate 308 and the foam compressive material 304 are a plurality of top markers arranged in rows parallel to the chest wall. The first row of top markers 306 is depicted closest to the chest wall, for example, proximate a front surface of the rigid substrate 308 and the foam compressive element 304. A second row of top markers 310 is disposed a first distance d1 from the first row 306, while a third row of top markers 312 is disposed a second distance d2 from the second row 310. The top markers 306, 310, 312 may be secured to the rigid substrate 308 or the foam compressive material 304 and may be disposed between those elements. In another example, the top markers may be disposed on an upper surface of the rigid substrate. In such locations, the top markers 306, 310, 312 primarily indicate the level of the top surface of the foam compressive material 304, as well as the bottom surface of the rigid substrate 308. The top markers 306, 310, 312 act as a fixed reference.

Secured to a bottom surface of the foam compressive material 304 are a plurality of bottom markers arranged in rows parallel to the chest wall. The first row of bottom markers 314 are depicted closest to the chest wall, for example, spaced a third distance d3 a front surface of the rigid substrate 308 and the foam compressive element 304. A second row of bottom markers 316 is disposed a fourth distance d4 from the first row 314, while a third row of bottom markers 318 are disposed a fifth distance d5 from the second row 316. The bottom markers 314, 316, 318 may be exposed at the bottom of the foam compressive material 304a, as depicted in FIG. 3A, or may be covered by a thin foam cover 320b, as depicted in FIG. 3B. The thin foam cover 320b may be formed from the same material, or a different material as the foam compressive material 304, and may be about 5%, about 7%, about 10%, about 12%, about 15%, or about 17% of the thickness of the foam compressive material 304. In this location, the bottom markers 314, 316, 318 primarily indicate the level of the top surface of the compressed breast, or the bottom surface of the foam compressive material 304 (for portions of the foam compressive material 304 not in contact with the breast).

The distances d1, d2, d3, d4, d5 allow each of the rows 306, 310, 312, 314, 316, 318 to be visible in a resulting image generated by emission from an x-ray tube (the focal spot thereof depicted at 320). Thus, given the angle of x-ray energy 322, the second bottom row of markers 316 would still be visible in the resulting image, due to the separation distance d2 between the second top row of markers 310 and the third top row of markers 312. The distances d1, d2, d3, d4, d5 may be determined based at least in part on the thickness of the foam compressive material 304, the length of the individual markers in each row of markers (described in more detail herein), the anticipated distance between the focal spot 322 and the markers, and other factors.

Figure 4A:
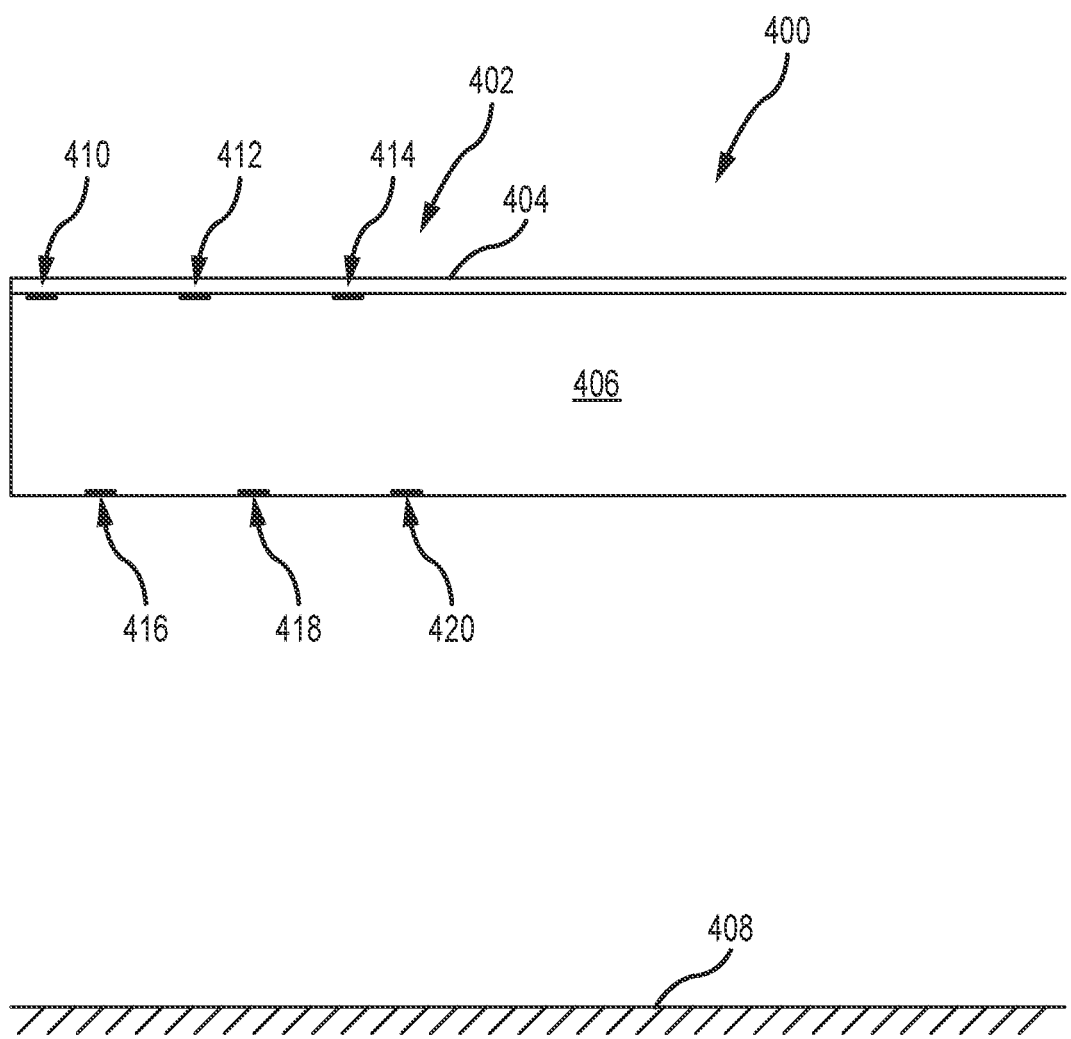
FIG. 4A depicts a partial side view of an imaging system having a paddle utilizing a foam compressive element and markers thereon, in an uncompressed position.

FIG. 4A depicts a partial side view of an imaging system 400 having a paddle 402 utilizing a foam compressive element 406 and markers thereon, in an uncompressed position. FIG. 4B depicts a top view of an image of the paddle 402 of FIG. 4A, in an uncompressed position. When imaged, all of the markers appear on a single depicted plane. FIGS. 4A and 4B are described concurrently. The foam compressive material 406 is secured to a rigid substrate 404 and is movably positionable relative to a breast support platform 408, as known in the art. Rows of top markers 410, 412, 414 are depicted, each of which include a number of discrete lines, tick marks, or other markings of known dimensions and separations. For example, each line of each row 410, 412, 414 has a known length $l_T$. Further, the distance between adjacent rows 410, 412, 414 is also known. Rows of bottom markers 416, 418, 420 are also depicted, and each include a number of discrete lines, tick marks, or other markings of known dimensions and separations. For example, each line of each row 410, 412, 414 has a known length $l_B$. Further, the distance between adjacent rows 410, 412, 414 is also known. When an x-ray image is taken of the paddle 402, the distance between adjacent rows (as depicted in the resulting image, e.g., of FIG. 4B) can be determined as D. Here, distance D is not necessarily identical between all the projections of all rows, but is merely utilized for illustrative purposes.

Figure 5A:
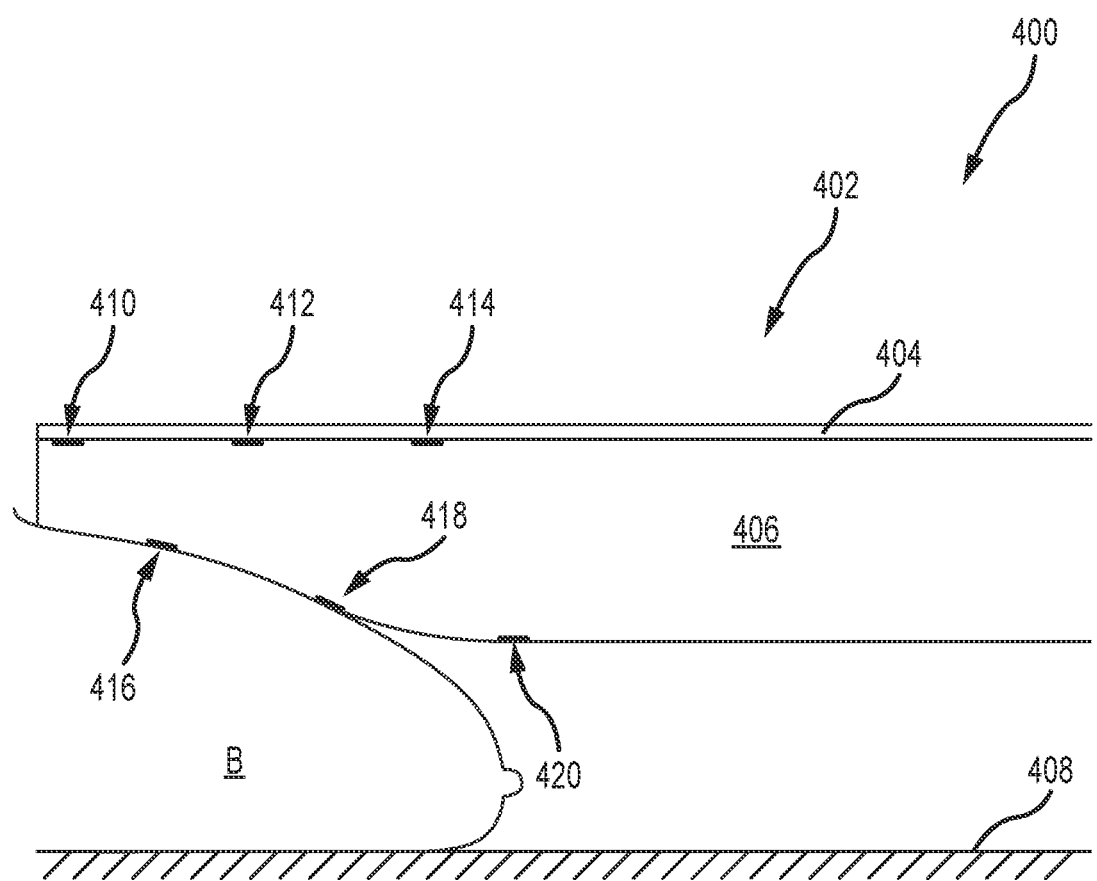
FIG. 5A depicts a partial side view of the imaging system of FIG. 4A, in a compressed position.
Figure 5B:
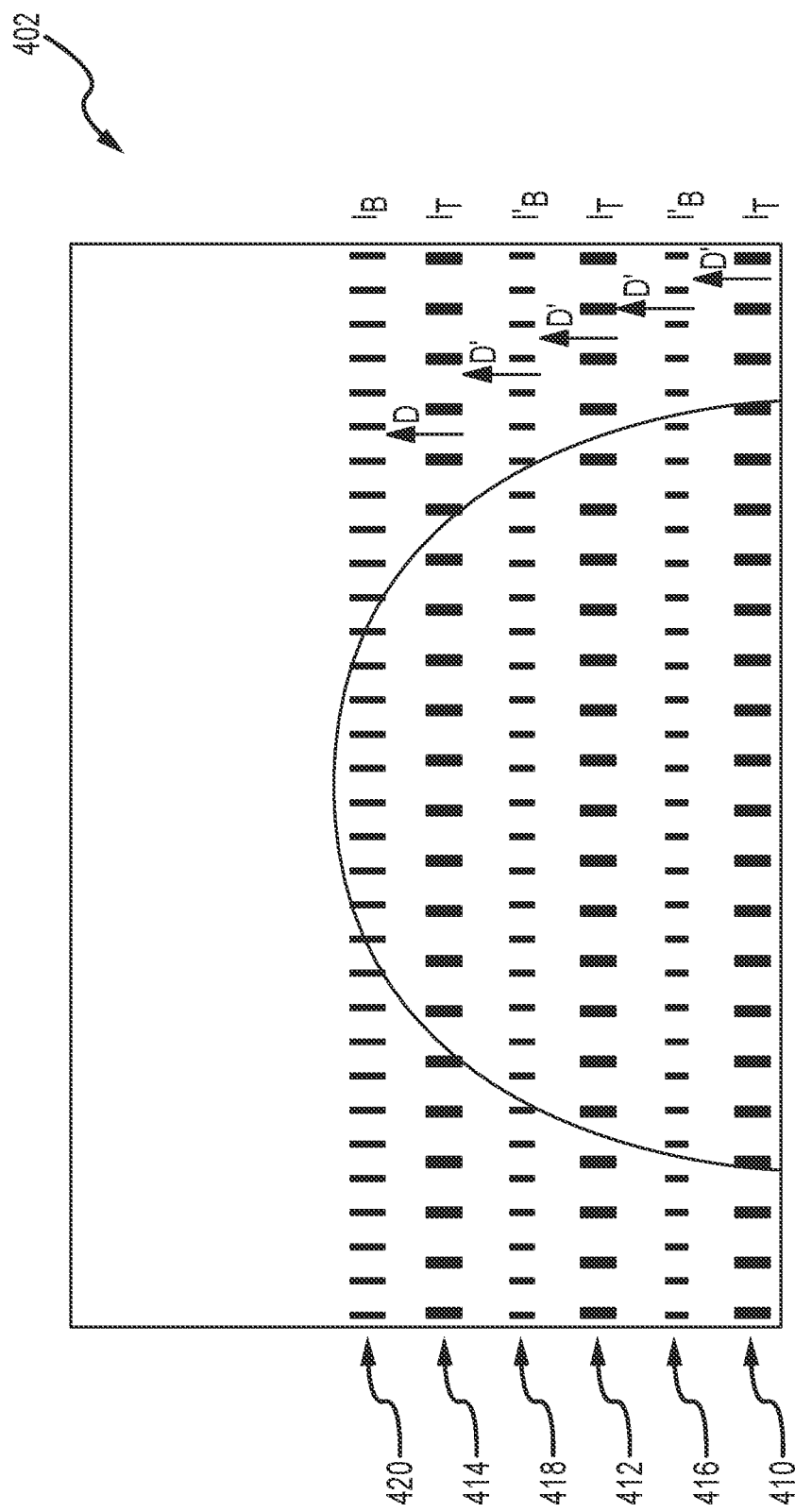
FIG. 5B depicts a top view of an image of the paddle of FIG. 5A, in a compressed position.

FIG. 5A depicts a partial side view of the imaging system 400 of FIG. 4A, in a compressed position. FIG. 5B depicts a top view of an image of the paddle 402 of FIG. 5A, in a compressed position. When imaged, all of the markers appear on a single depicted plane. FIGS. 5A and 5B are described concurrently. Certain components depicted in FIGS. 4A and 4B are also depicted in FIGS. 5A and 5B and, as such, are not necessarily described further. The foam compressive material 406 compresses a breast B against a breast support platform 408. During compression, the top markers 410, 412, 414 generally maintain their position and projected length $l_T$. This compression, however, changes either or both of the position and projected length of the bottom markers 416, 418, as the foam compressive element 406 changes shape to contour to the compressed breast B. In the projection of FIG. 5B, then, these changes are depicted as a changed separation distance D' between adjacent projected rows. Here, distance D' is not necessarily identical between all the projections of all rows, but is merely utilized for illustrative purposes. Notably, however, since the position of marker row 420 is unchanged (in that it is not located on a deflecting portion of the foam compressive material 406), the separation distance with adjacent top marker row 414 is unchanged from that in FIG. 4B. Further, the projected length of bottom marker rows 416, 418 is also changed, due to the change in curvature of the foam compressive material (this changed projected length is depicted as $l'_B$). Since marker row 420 is not located on a deflecting portion of the foam compressive material 406, its length remains as $l_B$. With these changes in marker lengths and marker separations known, geometric calculations allow the system to determine the curvature of the foam compressive material 406, and therefore information about the thickness of the breast located beneath each marker.

It can be appreciated that, if the length $l_T$, $l_B$ and separation distance D of markers depicted in FIGS. 4A and 5A are known, and the length $l'_T$, $l'_B$ and separation distance D' of imaged markers are measured in the x-ray image, trigonometric calculations can yield the distance between actual markers 410-420 and the imaging plane. The distance between markers 410, 412, 414 and the bottom of rigid substrate 404, and the distance between the imaging plane and the top of breast platform are known. By measuring the separation distances between projected adjacent rows of markers (e.g., top marker row 410 and bottom marker row 416), and the lengths of the bottom marker rows 416, 418, 420, the deflection of the bottom surface of the foam compressive material 406 can be determined. These various calculations are utilized to calculate the geometric thickness of compressed breast B at a significant number of locations to generate a profile of the compressed breast. Techniques for calculating the thickness of a breast compressed by a rigid paddle are described in U.S. Pat. No. 8,768,026, the disclosure of which is hereby incorporated by reference herein in its entirety. Those techniques address measuring the separation distance between adjacent markers in a single row to determine breast paddle height and, as a result, breast thickness. Those techniques are applicable for determining the distance of the top markers 410, 412, 414 above the breast support platform.

It has been discovered that the methods described in U.S. Pat. No. 8,768,026 may be modified and applied so as to calculate the separation distances D, D' between adjacent imaged rows, as well as lengths $l_T$, $l_B$, $l'_B$ of discrete markers in rows. With these calculations, breast thickness at a plurality of discrete points of the foam compressive material may be determined.

Figure 6:
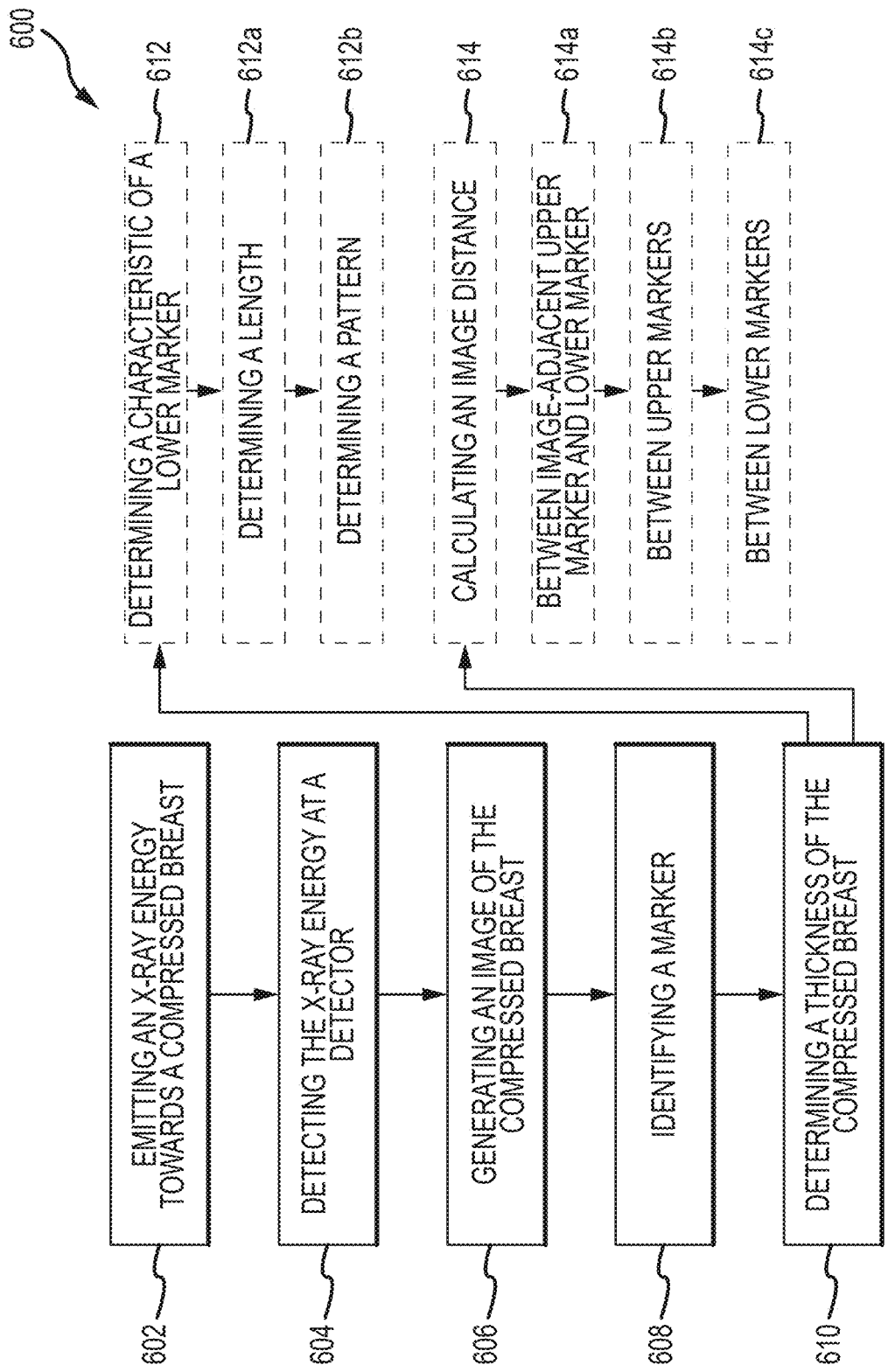
FIG. 6 depicts a method of imaging a breast compressed with a foam paddle.

More generally, FIG. 6 depicts a method 600 of imaging a breast compressed with paddle having a flexible compressive element, such as a foam compressive material. The method 600 begins with operation 602, emitting an x-ray energy from an x-ray source towards the breast and the foam paddle. The foam paddle may be configured as depicted elsewhere herein and includes, at a minimum, a plurality of upper markers and a plurality of lower markers. Since the lower markers are disposed proximate a lower surface of the foam paddle, the lower markers are movable relative to the upper markers, which stay fixed since they are typically disposed adjacent a rigid substrate of the foam paddle. In operation 604, the x-ray energy is detected at a detector disposed opposite the breast from the x-ray source (e.g., below a breast support platform). This detection may be a single detection (e.g., in the context of standard mammogram exposure or a scout image exposure) or there may be multiple detections (e.g., in the context of a tomosynthesis procedure). In operation 606, an image of the compressed breast based on the detected x-ray energy is generated. In operation 608, at least one of the plurality of upper markers and at least one of the plurality of lower markers is identified in the image generated in operation 606.

When this method 600 is utilized in a tomosynthesis imaging procedure, it may be applied to each of the tomosynthesis projection images to perform the thickness analysis. In that regard, the method 600 may be applied to 2D images generated during a standard mammogram, as well as the individual 2D images obtained during a tomosynthesis imaging procedure. In a tomosynthesis procedure, however, another method of analysis may be used to derive thickness information. Each slice may be reviewed and a slice with a stronger marker signal may be identified. The number of the slice in the stack of slices allows a determination of the height of the slice, which may be used to calculate the vertical (e.g., Z-axis) locations of the top and bottom markers. By identifying the slice with the strongest marker signal, markers will appear in a few slices instead of a single slice, but the slice with strongest signal corresponds to that slice's vertical location in the Z axis.

Returning to the method 600, operation 610 may determine a thickness of the compressed breast at a plurality of thickness locations. Each of the plurality of thickness locations corresponds to at least one of the plurality of lower markers. By determining the thickness of the breast (e.g., a height of the top of the breast above the breast platform), a complete profile of the upper surface of the breast may be generated.

A number of operations to calculate the breast thickness are depicted in the method 600. In some examples, generally only a single one of these operations need be utilized to determine the breast thickness. However, multiple operations are typically desired to increase the accuracy of the profile generated, which leads to improved performance and more accurate calculations in downstream processes (described further herein). For context, operation 618, determining or calculating image distance (e.g., a distance as depicted in an x-ray image) between upper markers is utilized to determine a height of the upper markers (disposed proximate the rigid substrate of the paddle), is described in U.S. Pat. No. 8,768,026, the disclosure of which is incorporated by reference herein in its entirety. This calculation provides baseline or datum information regarding the height of the rigid portion of the paddle and may be used in conjunction with other calculations described herein. Breast thicknesses at discrete locations may be calculated based on determinations or calculations regarding either or both of the characteristics of a marker (e.g., operation 612) and a separation distance between two markers (e.g., operation 614). For example, determining the thickness may include calculating a length, in the image, of at least one lower marker of the plurality of lower markers, operation 612a. Since the length of the lower markers are known, a change in that length (as reflected in the image) can aid in determining the amount of distance the foam compressive element has deformed. This deformation will cause the individual markers to appear shortened in the resulting image. In operation 612b, a resulting pattern of a marker may be determined and compared to the marker's known pattern. For example, if the marker is a dashed line and the frequency of dashes is changed in the resulting image, a deflection of that part of the foam compressive material may be determined.

With regard to calculating a distance in an image, operation 614, a number of calculations or determinations are depicted. In operation 614a, determining the thickness comprises calculating a separation distance, in the image, between a first upper marker of the plurality of upper markers and an image-adjacent first lower marker of the plurality of lower markers. Here, the term "image-adjacent" is used to indicate that in the image, upper and lower markers will appear in the same two-dimensional image, even though they are located at different heights of the paddle. A change in the separation distance from the known separation distance (e.g., when the paddle is in an uncompressed condition), indicates that the lower marker has moved relative to the upper marker. From this information, geometric calculations may be performed to associate the change in separation distance with a change in height of the second marker. In operation 618b, determining the thickness includes calculating a distance, in the image, between a first upper marker of the plurality of upper markers and a second upper marker of the plurality of upper markers. Again, this is described in U.S. Pat. No. 8,768,026. In operation 614c, determining the thickness comprises calculating a separation distance, in the image, between a first lower marker of the plurality of lower markers and a first lower marker of the plurality of lower markers. An apparent change in said separation distance is indicative of the plurality of lower markers being at a different elevation and consequentially, above a portion of the breast having a different thickness than another portion. Once the thickness is determined, further methods may be performed to properly image the breast, generate images for display, eliminate artifacts, etc., as described below.

Figure 6A:
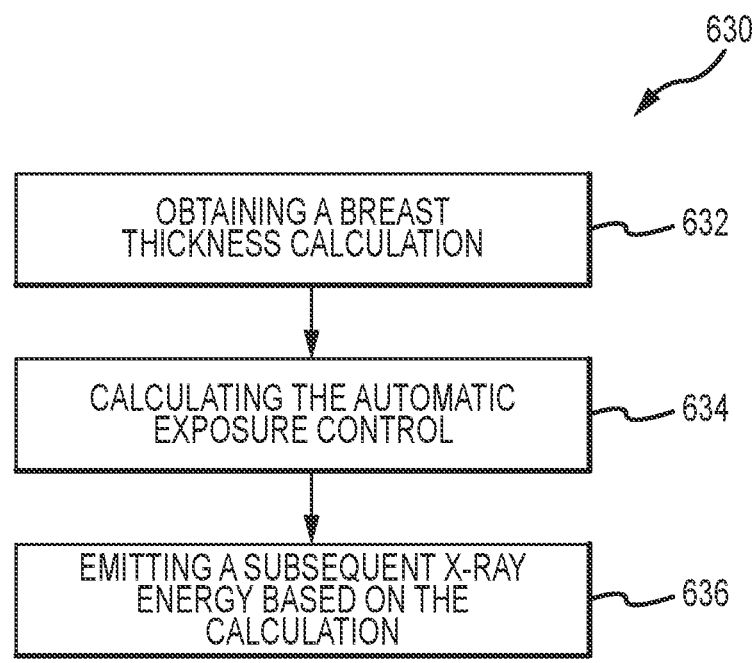
FIG. 6A depicts a method of calculating automatic exposure control utilizing the breast thickness calculations made in the method of FIG. 6.

FIG. 6A depicts a method 630 of calculating automatic exposure control (AEC) utilizing the breast thickness calculations made in the method 600 of FIG. 6. Calculation of automatic exposure control requires breast thickness as an input. Operation 632 obtains the breast thickness calculation, e.g., for example from the method 600. In this method 630, the breast thickness may be calculated in the method 600 from a scout exposure (e.g., the emitted x-ray energy). Based on the thickness, operation 634 calculates the AEC. One or more factors may be utilized or considered in calculating AEC for a non-uniformly compressed breast. In examples, a volume of the breast (which may be calculated based on the determined profile of the breast) pay be considered. In another example, a thickness of the breast at a particular location (e.g., proximate the chest wall or proximate the nipple) may be considered. In another example, an average thickness of the breast across an area thereof may be considered. In still another example, AEC may be calculated for one or more discrete portions of the breast (e.g., proximate one or more of the chest wall, nipple, or other location). Those resulting AECs may be further considered or weighted to determine AEC for the breast as a whole. In examples, multiple considerations may be utilized. Once this AEC is known, a subsequent imaging x-ray emission (e.g., a standard mammogram and/or a tomosynthesis scan) may be emitted, operation 636. The dose of that subsequent x-ray emission is based at least in part on the calculated automatic exposure control.

Figure 6B:
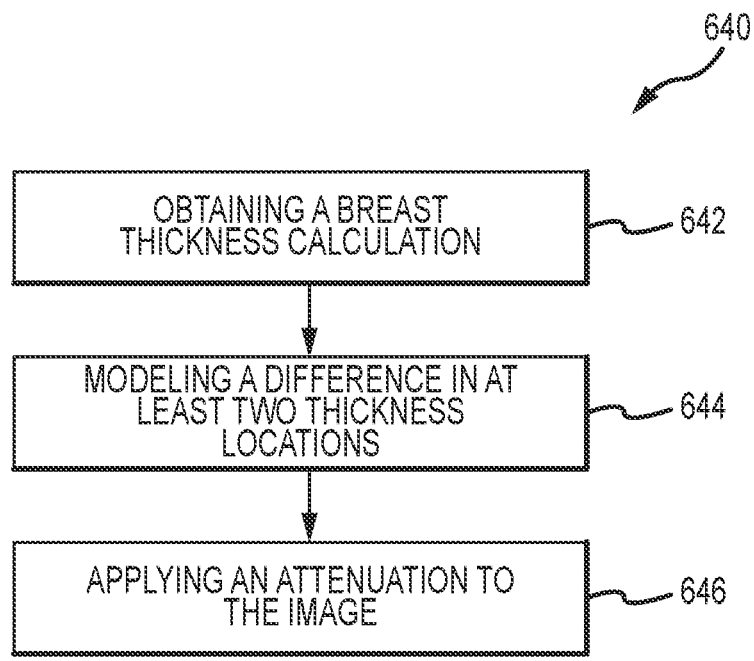
FIG. 6B depicts a method of equalizing an image of the compressed breast utilizing the breast thickness calculations made in the method of FIG. 6.

FIG. 6B depicts a method 640 of equalizing an image of the compressed breast utilizing the breast thickness calculations made in the method 600 of FIG. 6. When a breast under compression does not have uniform thickness, the resulting x-ray image would appear non-flat after standard image processing. This non-flatness can make review of a mammogram image difficult, since a breast image needs to appear flat for proper lesion identification. In general, there are few, if any, efficient image processing methods to flatten a breast image of irregular thickness. However, if a breast thickness profile is known (e.g., via the method 600 of FIG. 6), the physical thickness change of the breast may be modeled. Additional tissue attenuation may then be utilized to compensate the image of the breast. The resultant breast image will appear as if the image was of a breast of uniform thickness. Known image processing algorithms may then be utilized to produce a diagnostically-relevant image for review. In this method 640, the breast thickness may be calculated in the method 600, and obtained therefrom, operation 642. Based on the thickness as varied across the entire breast a profile of the breast may be constructed. A difference in breast thickness in at least two different thickness locations may be modeled, operation 644. The model utilized determines which portions of the breast should be attenuated (and by how much) so as to flatten the appearance of the breast in the image. Based on the modeled difference, attenuation may be applied to the breast, operation 646.

Figure 6C:
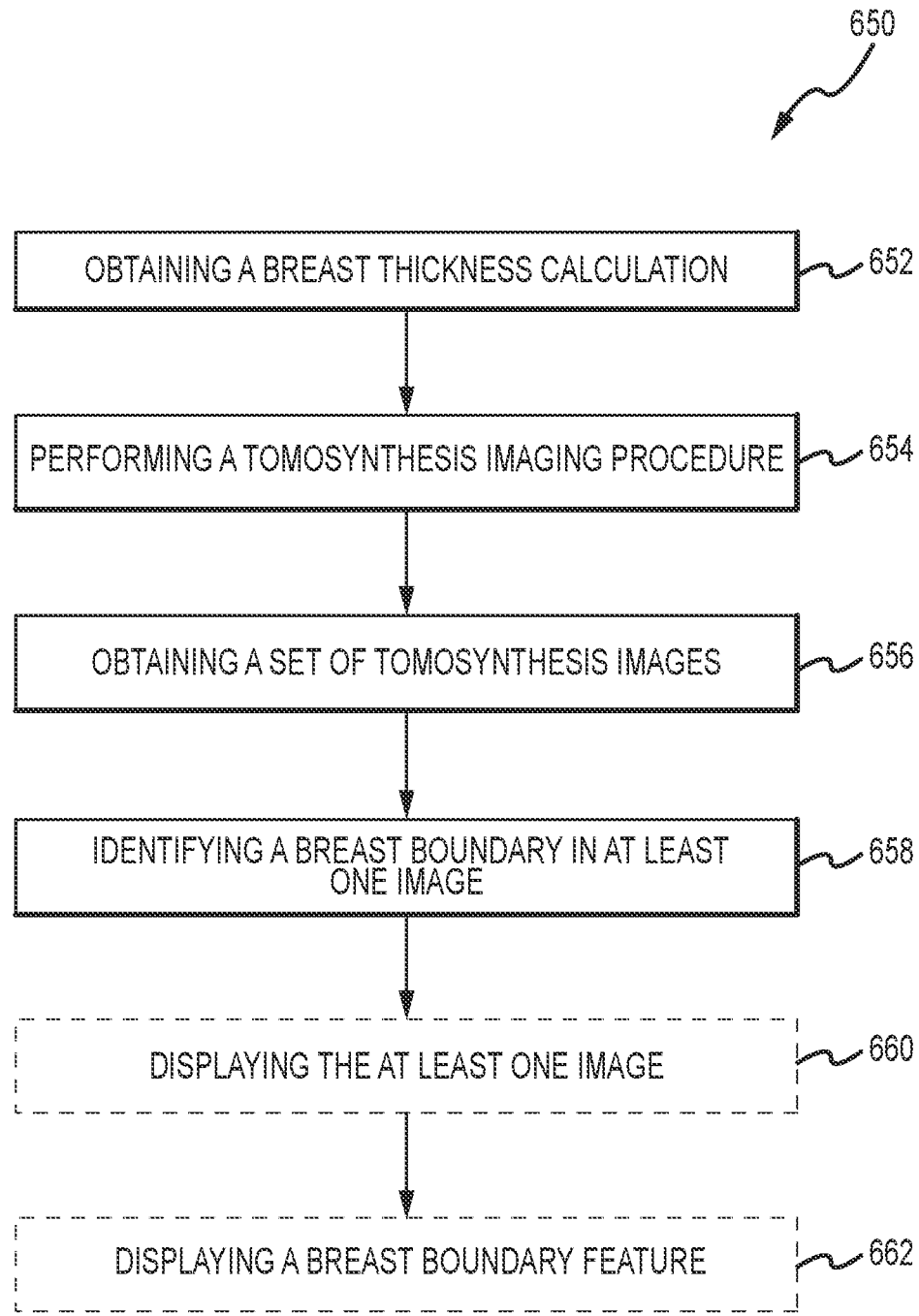
FIG. 6C depicts a method of identifying a breast boundary of the compressed breast utilizing the breast thickness calculations made in the method of FIG. 6.

FIG. 6C depicts a method 650 of identifying a breast boundary of the compressed breast utilizing the breast thickness calculations made in the method 600 of FIG. 6. In a tomosynthesis image set, the last slice of reconstructed breast volume often lacks a clear indication of the breast boundary due to limited Z-axis resolution. The problem is exacerbated when a paddle having a foam compressive element is utilized, because the physical breast boundary can locate across more than one slice (in fact, several slices are often effected). Since the proposed technologies accurately measure breast thickness within the field of view, that thickness information may be utilized to identify the breast boundary. Additional software may be utilized to digitally label the boundary of breast volume in each reconstruction slice. This helps save time for the image stack reviewer (e.g., a clinician), since she will not now have to review portions of the slice disposed outside the breast volume. In this method 650, the breast thickness may be calculated in the method 600, and obtained therefrom, operation 652. In operation 654, a tomosynthesis imaging procedure is performed. In an example, the tomosynthesis imaging procedure performed may be the x-ray energy emitted as operation 602 of method 600. In another example, the tomosynthesis imaging procedure may be discrete therefrom. In operation 656, a set of tomosynthesis images of the compressed breast is obtained from the tomosynthesis imaging procedure. In operation 658, a breast boundary is identified in at least one tomosynthesis image of the set of tomosynthesis images; often, this boundary will be identified in multiple slices, often one or more of the uppermost slices, based at least in part by the thickness determination.

In an example, the boundary may be identified by comparing the thickness of the breast at multiple discrete locations to the various slices generated. The thickness at these multiple discrete locations corresponds to the upper contour or vertical boundary (e.g., the uppermost skin surface) of the breast. Thus, all portions of the slice that lie outside of the thickness of the breast at each particular location may be excluded from further processing and/or display. In operations 660 and 662, respectively, display of the slice(s) and the breast boundary is performed. In operation 660 specifically, at least one tomosynthesis image of the set of tomosynthesis images is displayed. In operation 662, a feature indicative of the breast boundary is displayed on the displayed tomosynthesis image(s). This boundary may be line, contour, or curve surrounding the relevant area. In other examples, all areas outside the breast boundary may be blocked, covered, or otherwise distorted. In another example, the portions of the image outside the breast boundary may be entirely eliminated from display.

Figure 6D:
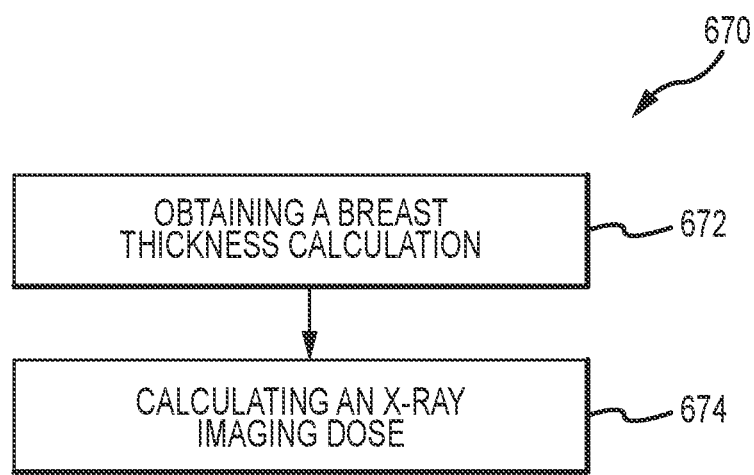
FIG. 6D depicts a method of calculating an x-ray imaging dose for imaging the compressed breast utilizing the breast thickness calculations made in the method of FIG. 6.

FIG. 6D depicts a method 670 of calculating an x-ray imaging dose for imaging the compressed breast utilizing the breast thickness calculations made in the method 600 of FIG. 6. Without breast thickness as input, x-ray radiation dose cannot be calculated correctly. In this method 670, the breast thickness may be calculated in the method 600, and obtained therefrom, operation 672. In operation 674, the x-ray imaging dose may be calculated based thereon. In examples, dose correction factors may be applied, or the dose may be based on a local thickness (e.g., proximate a particular portion of the breast), or the dose may be based on a calculated average across the entire thickness of the breast, based on area.

Figure 6E:
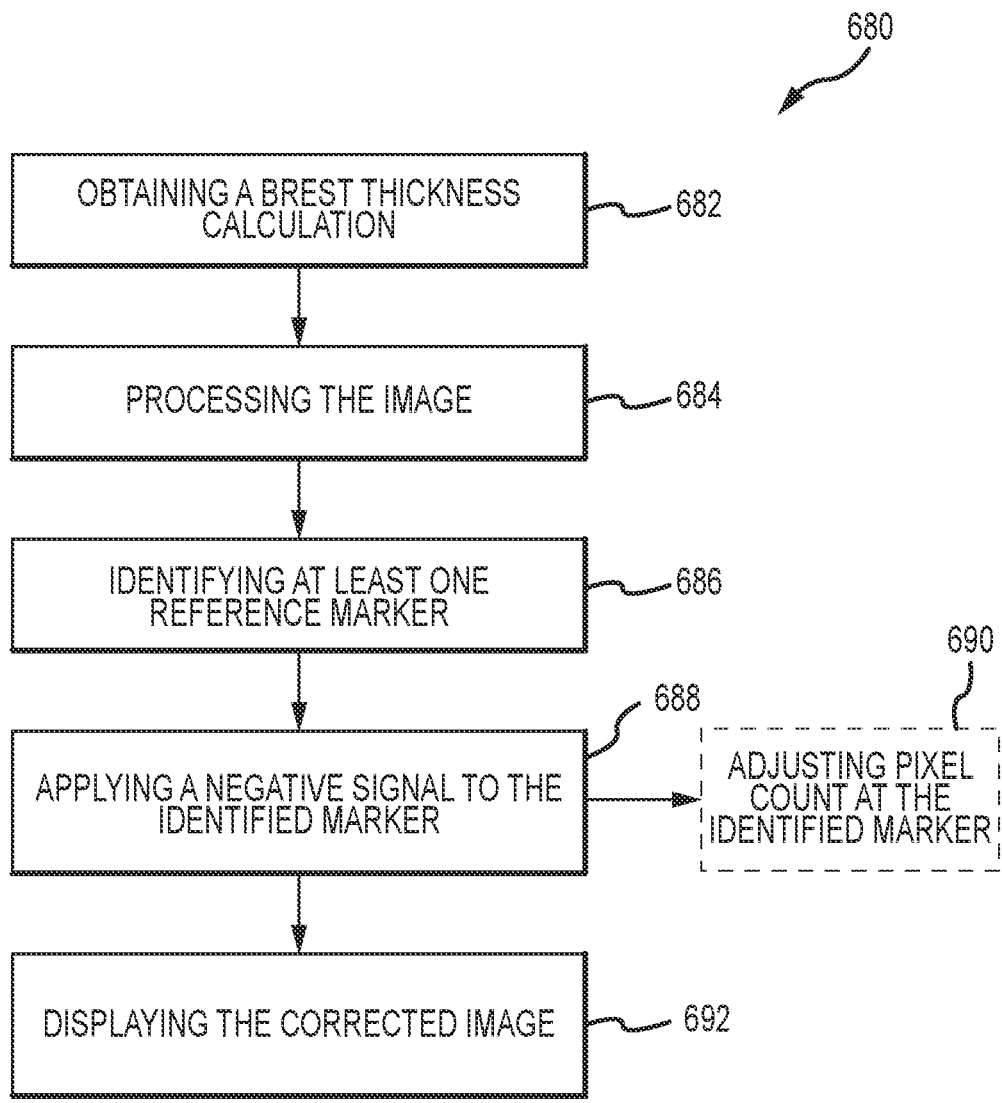
FIG. 6E depicts a method of reducing marker artifacts in the image of the compressed breast utilizing the breast thickness calculations made in the method of FIG. 6.

FIG. 6E depicts a method 680 of reducing marker artifacts in the image of the compressed breast utilizing the breast thickness calculations made in the method 600 of FIG. 6. In this method 680, the markers are chosen such that they are not visible in normal breast images and they become visible only after supplemental image processing. After image processing, the upper marker and lower marker intensities and their locations in the images are known. Negative marker signals may then be added to the image, so as to render the image marker artifact-free. This is particularly important for quality control images of the system. In this method 680, the breast thickness may be calculated in the method 600, and obtained therefrom, operation 682. In operation 684, the image is processed via known processing techniques. In operation 686, at least one reference marker of at least one of the plurality of upper markers and the plurality of lower markers is identified in the image. In operation 688, a negative signal is applied to the identified reference marker; this application results in a corrected image. In an example, the negative signal may correspond to an adjustment of pixel counts at the location of the identified marker, operation 690. These identification and application operations may be performed on the entire image, so as to effectively remove the marker artifacts therefrom. In other examples, only markers located within the breast boundary (e.g., as identified in the method 650 of FIG. 6C) may be so identified. In operation 692, the corrected image is displayed.

Figure 7:
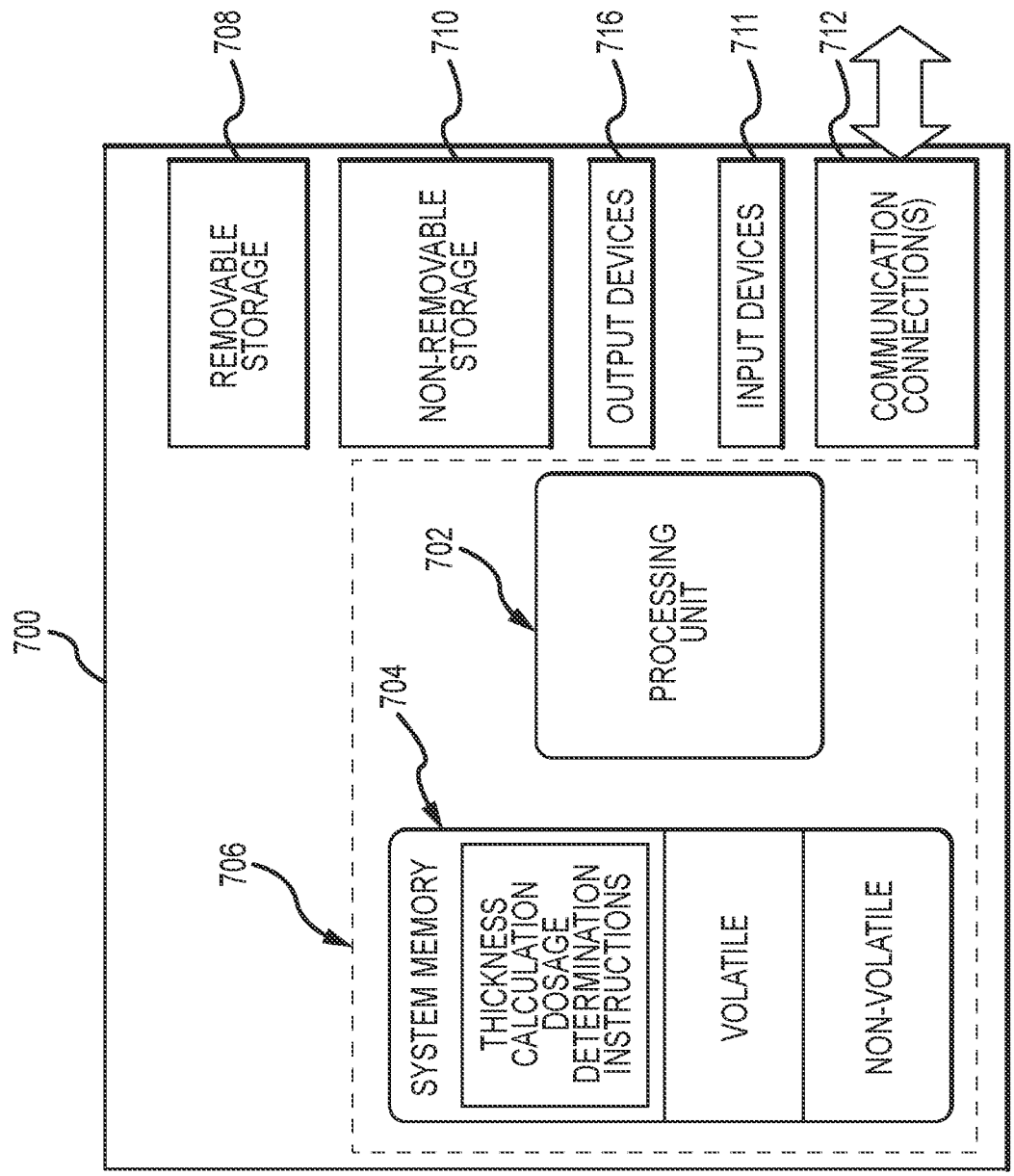
FIG. 7 depicts an example of a suitable operating environment in which one or more of the present examples can be implemented.

FIG. 7 illustrates one example of a suitable operating environment 700 in which one or more of the present examples can be implemented. This operating environment may be incorporated directly into the imaging systems disclosed herein, or may be incorporated into a computer system discrete from, but used to control, a the imaging and compression systems described herein. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 700 typically includes at least one processing unit 702 and memory 704. Depending on the exact configuration and type of computing device, memory 704 (storing, among other things, instructions to calculate breast thickness, determine x-ray dosages, or perform other methods disclosed herein) can be volatile (such as RAM), non-volatile (such as ROM, flash memory, etc.), or some combination of the two. This most basic configuration is illustrated in FIG. 7 by dashed line 706. Further, environment 700 can also include storage devices (removable, 708, and/or non-removable, 710) including, but not limited to, magnetic or optical disks or tape. Similarly, environment 700 can also have input device(s) 714 such as touch screens, keyboard, mouse, pen, voice input, etc., and/or output device(s) 716 such as a display, speakers, printer, etc. Also included in the environment can be one or more communication connections 712, such as LAN, WAN, point to point, Bluetooth, RF, etc.

Operating environment 700 typically includes at least some form of computer readable media. Computer readable media can be any available media that can be accessed by processing unit 702 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 700 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein include such modules or instructions executable by computer system 700 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 700 is part of a network that stores data in remote storage media for use by the computer system 700.

Figure 8:
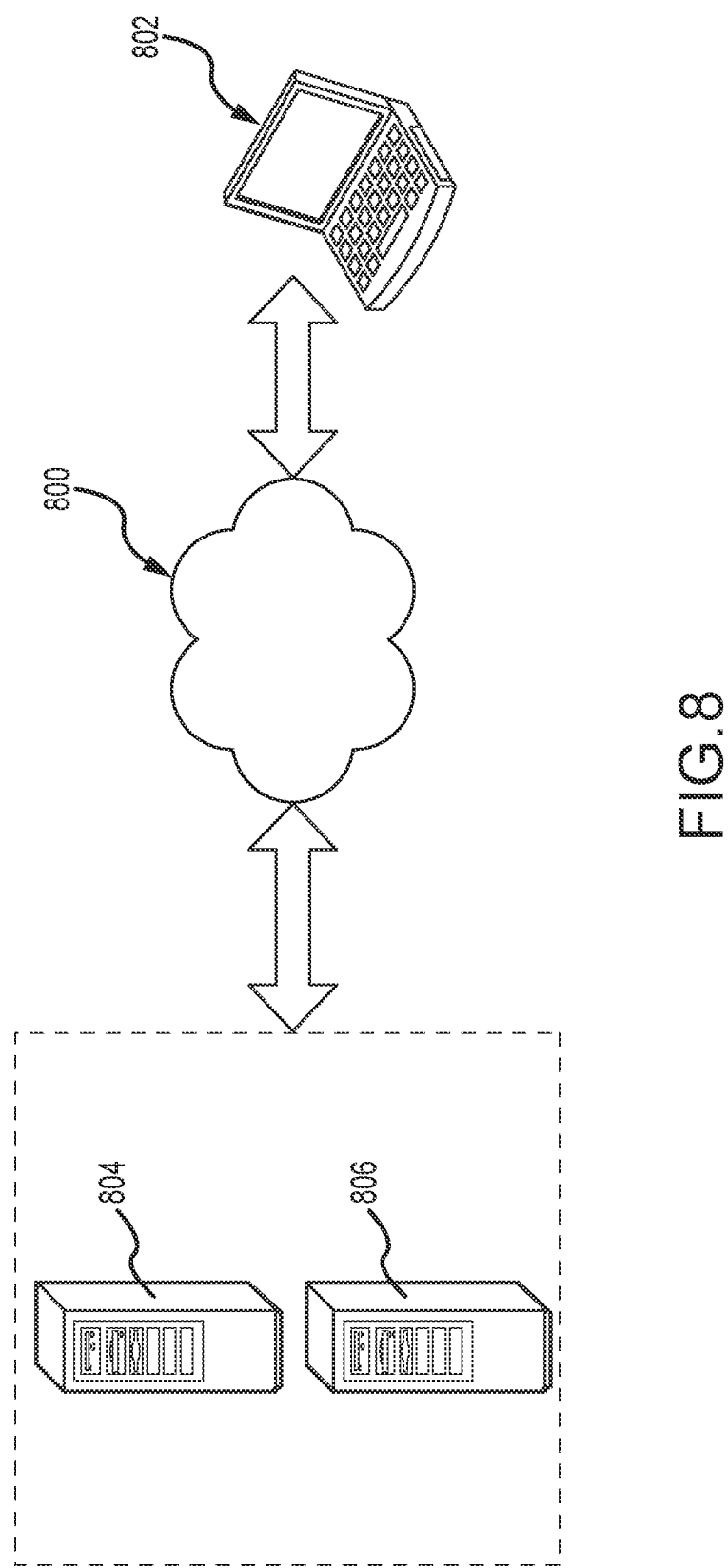
FIG. 8 depicts an example of a network in which the various systems and methods disclosed herein may operate.

FIG. 8 is an embodiment of a network 800 in which the various systems and methods disclosed herein may operate. In embodiments, a client device, such as client device 802, may communicate with one or more servers, such as servers 804 and 806, via a network 808. In embodiments, a client device may be a standalone imaging system (e.g., imaging system 120 depicted in FIG. 1A) that includes all the functionality described herein. The client device may also include or incorporate a laptop, a personal computer, a smart phone, a PDA, a netbook, or any other type of computing device, such as the computing device in FIG. 7. In examples, such a client device may be connected to an imaging system. In embodiments, servers 804 and 806 may also be any type of computing device, such as the computing device illustrated in FIG. 7. Network 808 may be any type of network capable of facilitating communications between the client device and one or more servers 804 and 806. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In embodiments, the various systems and methods disclosed herein may be performed by one or more server devices. For example, in one embodiment, a single server, such as server 804 may be employed to perform the systems and methods disclosed herein, such as the methods for imaging discussed herein. Client device 802 may interact with server 804 via network 808. In further embodiments, the client device 802 may also perform functionality disclosed herein, such as scanning and image processing, which can then be provided to servers 804 and/or 806.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of imaging a breast compressed with a foam paddle, the method comprising:
    emitting an x-ray energy from an x-ray source towards the breast and the foam paddle having a plurality of upper markers and a plurality of lower markers, wherein the plurality of lower markers are movable relative to the plurality of upper markers;
    detecting the x-ray energy at a detector disposed opposite the breast from the x-ray source;
    generating an image of the compressed breast based on the detected x-ray energy;
    identifying, in the image, at least one of the plurality of upper markers and at least one of the plurality of lower markers; and
    determining a thickness of the compressed breast at a plurality of thickness locations, wherein each of the plurality of thickness locations corresponds to at least one of the plurality of lower markers.

2. The method of claim 1, wherein determining the thickness comprises calculating a distance, in the image, between a first upper marker of the plurality of upper markers and an image-adjacent first lower marker of the plurality of lower markers.

3. The method of claim 1, wherein determining the thickness comprises determining a characteristic, in the image, of at least one lower marker of the plurality of lower markers.

4. The method of claim 1, wherein determining the thickness comprises calculating a distance, in the image, between a first upper marker of the plurality of upper markers and a second upper marker of the plurality of upper markers.

5. The method of claim 1, wherein determining the thickness comprises calculating a distance, in the image, between a first lower marker of the plurality of lower markers and a second lower marker of the plurality of lower markers.

6. The method of claim 1, wherein the x-ray energy comprises a scout exposure.

7. The method of claim 6, further comprising calculating an automatic exposure control based at least in part on the determination of the thickness.

8. The method of claim 7, further comprising emitting an imaging x-ray energy based at least in part on the calculated automatic exposure control.

9. The method of claim 1, further comprising:
    modeling a difference in at least two thickness locations of the plurality of thickness locations; and
    applying attenuation to the image based at least in part of the modeled difference.

10. The method of claim 1, further comprising:
    performing a tomosynthesis imaging procedure;
    obtaining a set of tomosynthesis images of the compressed breast from the tomosynthesis imaging procedure; and
    identifying a breast boundary in at least one tomosynthesis image of the set of tomosynthesis images.

11. The method of claim 10, wherein identifying the breast boundary is based at least in part on the determination of the thickness.

12. The method of claim 11, further comprising:
    displaying at least one tomosynthesis image of the set of tomosynthesis images; and displaying, on the displayed at least one tomosynthesis image of the set of tomosynthesis images, a feature indicative of the breast boundary.

13. The method of claim 12, wherein the displayed at least one tomosynthesis image comprises an uppermost tomosynthesis image of the breast.

14. The method of claim 1, further comprising calculating an x-ray imaging dose based at least in part on the determination of the thickness.

15. The method of claim 1, further comprising:
processing the image;
identifying at least one reference marker of at least one of the plurality of upper markers and the plurality of lower markers;
applying a negative signal to the identified reference marker, wherein the application results in a corrected image; and
displaying the corrected image.

16. The method of claim 15, wherein applying the negative signal comprises adjusting a pixel count at the identified reference marker.

17. A paddle for compressing a breast, the paddle comprising:
a foam profile comprising an upper surface, a lower surface, and a front wall;
a plurality of upper markers disposed proximate the upper surface, wherein the plurality of upper markers are disposed a first distance from the front wall; and
a plurality of lower markers disposed proximate the lower surface, wherein the plurality of lower markers are disposed a second distance from the front wall, the second distance configured relative to the first distance such that movement of one or more of the plurality of lower markers is measurable relative to the plurality of upper markers.

18. The paddle of claim 17, further comprising a rigid substrate, wherein the foam profile is secured to the rigid substrate at the upper surface, and wherein the plurality of upper markers are disposed between the rigid substrate and the foam profile.

19. The paddle of claim 17, wherein the plurality of lower markers are disposed within the foam profile.

20. The paddle of claim 17, wherein the plurality of lower markers are configured to move when the lower surface of the paddle is acted upon by an upward force.

21. The paddle of claim 20, wherein the plurality of upper markers are configured to remain stationary when the lower surface of the paddle is acted upon by the upward force.

22. The paddle of claim 17, further comprising a bottom foam profile secured to the foam profile, wherein the plurality of lower markers are disposed between the bottom foam profile and the foam profile.

* * * * *